United States Patent
Thayumanavan et al.

(10) Patent No.: US 12,186,319 B2
(45) Date of Patent: Jan. 7, 2025

(54) CROSSLINKED POLYMER NANOPARTICLES FOR TARGETED CELLULAR UPTAKE AND THERAPEUTICS, AND COMPOSITIONS AND METHODS THEREOF

(71) Applicant: University of Massachusetts, Boston, MA (US)

(72) Inventors: Sankaran Thayumanavan, Amherst, MA (US); Lisa Minter, Southampton, MA (US)

(73) Assignee: University of Massachusetts, Boston, MA (US)

( * ) Notice: Subject to any disclaimer, the term of this patent is extended or adjusted under 35 U.S.C. 154(b) by 691 days.

(21) Appl. No.: 16/607,712

(22) PCT Filed: May 10, 2018

(86) PCT No.: PCT/US2018/031939
§ 371 (c)(1),
(2) Date: Oct. 23, 2019

(87) PCT Pub. No.: WO2018/209006
PCT Pub. Date: Nov. 15, 2018

(65) Prior Publication Data
US 2020/0113906 A1    Apr. 16, 2020

Related U.S. Application Data

(60) Provisional application No. 62/504,201, filed on May 10, 2017.

(51) Int. Cl.
*A61K 31/519* (2006.01)
*A61K 47/36* (2006.01)
*C08B 37/08* (2006.01)

(52) U.S. Cl.
CPC ............ *A61K 31/519* (2013.01); *A61K 47/36* (2013.01); *C08B 37/0072* (2013.01)

(58) Field of Classification Search
CPC .................................................. A61K 31/519
See application file for complete search history.

(56) References Cited

FOREIGN PATENT DOCUMENTS

WO    WO-2018037120 A1 *  3/2018  ............. A61P 29/00

OTHER PUBLICATIONS

Bianchin, Mariana, et al. "Radar charts based on particle sizing as an approach to establish the fingerprints of polymeric nanoparticles in aqueous formulations." Journal of Drug Delivery Science and Technology. (2015), vol. 30, pp. 180-189. (Year: 2015).*
Wei, Zhao, et al. "Dual Cross-Linked Biofunctional and Self-Healing Networks to Generate User-Defined Modular Gradient Hydrogel Constructs." Adv. Healthcare Mater. (2017), vol. 6, pp. 1-9 of 9. (Year: 2017).*
American Chemical Society. Chemical Abstract Service. RN 586348-25-6. Entered into STN/date first made available to public: Sep. 16, 2003. (Year: 2003).*

* cited by examiner

*Primary Examiner* — John S Kenyon
(74) *Attorney, Agent, or Firm* — Milstein Zhang & Wu LLC

(57) ABSTRACT

The invention provides novel compounds, pharmaceutical compositions and methods of preparation and therapeutic use thereof. The invention also provides novel gel compositions comprising hyaluronic acid (HA) polymers that are crosslinked with appropriate reversible crosslinkers and encapsulation of therapeutics or other payloads in such gel composition and nanoparticles thereof. The invention also relates to targeted delivery of such gel compositions and nanoparticles to specific cell types in a controllable delivery and release. The invention additionally relates to methods of therapeutic use of such gel compositions and nanoparticles in treatment of various diseases and conditions. The invention further relates to methods of preparation of the gel compositions and nanoparticles disclosed herein.

17 Claims, 19 Drawing Sheets

B

C

A

B

HA inhibitor Pep-1: 12-mer (GAHWQFNALTVR)peptide

HA microgel (Nile red) without inhibitor

HA microgel (Nile red) with inhibitor

CROSSLINKED POLYMER NANOPARTICLES FOR TARGETED CELLULAR UPTAKE AND THERAPEUTICS, AND COMPOSITIONS AND METHODS THEREOF

PRIORITY CLAIMS AND RELATED PATENT APPLICATIONS

This application is the U.S. national phase of and claims priority to PCT/US18/31939, filed May 10, 2018, which claims the benefit of priority to U.S. Provisional Application Ser. No. 62/504,201, filed on May 10, 2017, the entire content of each of which is incorporated herein by reference.

TECHNICAL FIELDS OF THE INVENTION

The invention generally relates to compounds, polymers and nano-structures and therapeutic use thereof. More particularly and in various aspects, the invention relates to certain compounds, pharmaceutical compositions and methods of preparation and therapeutic use thereof. The invention also relates to gel compositions comprising hyaluronic acid (HA) polymers that are crosslinked with appropriate reversible crosslinkers and encapsulation of therapeutics or other payloads in such gel composition and nanoparticles thereof. The invention also relates to targeted delivery of such gel compositions and nanoparticles to specific cell types in a controllable delivery and release. The invention additionally relates to methods of therapeutic use of such gel compositions and nanoparticles in treatment of various diseases and conditions. The invention further relates to methods of preparation of the compounds, gel compositions and nanoparticles disclosed herein.

BACKGROUND OF THE INVENTION

Nanoparticles have had a significant impact on a variety of areas such as microelectronics, multiphase catalysis, sensing and therapeutics. For most applications, facile modulation of the nanoparticle surface is critical in order to obtain appropriate interfacial properties. The ability to encapsulate and release guest molecules within the nanoparticle interior is also required for applications such as sensing and therapeutics. (*Nanoparticles: From Theory to Application*; Schmid, Ed.; Wiley-VCH: Essen, 2004; Zhang, et al. *Self-Assembled Nanostructures*; Nanostructure Science and Technology Series; Springer: 2002; *Nanoparticles: Building Blocks for Nanotechnology*; Rotello, Ed.; Springer: 2003; Daniel, et al. 2004 Chem. Rev. 104, 293.)

Polymer vesicles have been generated and extensively investigated as drug delivery vehicles, diagnostics, nanoreactors and artificial organelles. Potential advantages of polymer vesicles compared to their lipid counterparts arise from the enhanced colloidal stability, tunable membrane thickness and permeability, and engineered surface functionalities. A remaining challenge involves the unstable nature of the non-covalently organized supramolecular assembly of the polymer vesicles, which causes morphological changes. (Tanner, et al. 2011 *Acc. Chem. Res.* 44, 1039-1049; Vriezema, et al. 2007 *Angew. Chem. Int. Ed.* 46, 7378-7382; Wang, et al. 2012 Angew. Chem. Int. Ed. 51, 11122-11125; Lomas, et al. 2007 *Adv. Mater.* 19, 4238-4243; Choucair, et al. 2005 *Langmuir* 21, 9308-9313; Ben-Haim, et al. 2008 *Nano Lett.* 8, 1368-1373; Ghoroghchian, et al. 2005 *PNAS* 102, 2922-2927; Choi, et al. 2005 *Nano Lett.* 5, 2538-2542; Sanson, et al. 2011 *ACS Nano* 5, 1122-1140; Ahmed, et al. 2006 *J. Control. Releas.* 116, 150-158.)

Improved delivery methodologies are critical for polymer-based therapeutics. A number of disease conditions, such as inflammation and cancer, may be appropriately addressed using precise and controlled delivery techniques. For example, rheumatoid arthritis (RA) is a chronic inflammatory disorder that can affect primarily affects joints. RA typically results in warm, swollen, and painful joints. Unlike the wear-and-tear damage of osteoarthritis, RA affects the lining of your joints, causing a painful swelling that can eventually result in bone erosion and joint deformity. While the cause of RA is not clear, the underlying mechanism involves the body's immune system attacking the joints. It also affects the underlying bone and cartilage. In some patients, the condition also can damage a wide variety of body systems, including the skin, eyes, lungs, heart and blood vessels.

RA affects about 24.5 million people worldwide and exerts a heavy burden on the patient in terms of disability and on the healthcare system in terms of economic costs. Because RA tends to be progressive in nature and often begins for many people during the early or middle years of life, the disease often has a long-term impact on functioning (over 30 years for some patients), which produces a considerable social and economic cost.

Thus, there is an urgent need for improved therapeutics and delivery methodologies that allow efficient and precise delivery of therapeutic or other agents to the disease site.

SUMMARY OF THE INVENTION

The invention provides novel compounds, pharmaceutical compositions and methods of preparation and therapeutic use thereof. The invention also provides gel compositions comprising hyaluronic acid (HA) polymers that are crosslinked with appropriate reversible crosslinkers and encapsulation of therapeutics or other payloads in such gel composition and nanoparticles thereof. The invention also provides targeted delivery of such gel compositions and nanoparticles to specific cell types in a controllable delivery and release. The invention additionally provides to methods of therapeutic use of such gel compositions and nanoparticles in treatment of various diseases and conditions. The invention further provides to methods of preparation of the compounds, gel compositions and nanoparticles disclosed herein.

A key feature of the invention is a novel methodology for targeted delivery of a payload (e.g., therapeutic, diagnostic or imaging agents) to the intended location and for controlled release of the payload at the desired site resulting from partial or complete decrosslinking of the nanoparticles that is triggered by the local environment (e.g., redox- or pH-sensitive, degradable crosslinkers).

In one aspect, the invention generally relates to a gel composition comprising cross-linked hyaluronic acid, wherein the hyaluronic acid is cross-linked by one or more cross-linking groups that comprises structural formula I:

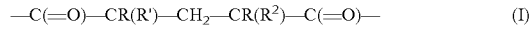
$$-C(=O)-CR(R')-CH_2-CR(R^2)-C(=O)- \qquad (I)$$

and one or more cross-linking groups that comprises structural formula II:

$$-CH_2-S-S-CH_2- \qquad (II)$$

wherein each of R, $R^1$ and $R^2$ is independently selected from the group consisting of H, a $C_1$-$C_{14}$ alkyl group, a $C_4$-$C_{14}$ aryl group, a halogen, or a bond linking the cross-linking group to the crosslinked hyaluronic acid network.

In certain embodiments of the gel composition, the hyaluronic acid is cross-linked by one or more cross-linking groups that comprises structural formula Ia:

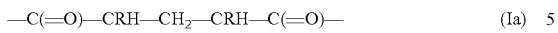   (Ia)

In certain embodiments of the gel composition, the one or more cross-linking groups that comprises structural formula II comprises formula III:

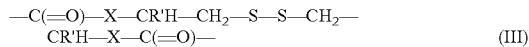   (III)

wherein each R' is H, —C(=O)O—R", or —C(=O)—NH—R", wherein R" is a group comprising a $C_1$-$C_{14}$ alkyl group or a $C_4$-$C_{14}$ aryl moiety; each X is independently selected from NH, O and S.

In certain embodiments, the one or more cross-linking groups that comprises structural formula III comprises formula IV:

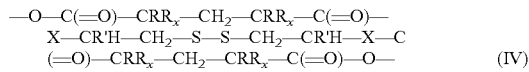   (IV)

wherein each $R_x$ independently represents a bond linking the cross-linking group to the crosslinked hyaluronic acid network; each X is independently selected from NH, O and S. In certain embodiments, each X is NH. In certain embodiments, each X is O. In certain embodiments, each X is S.

In yet another aspect, the invention generally relates to a pharmaceutical composition comprising a di-ester of methotrexate.

In yet another aspect, the invention generally relates to a method for controlled delivery of an agent to a target biological site. The method includes: providing a composition comprising a gel composition of cross-linked hyaluronic acid as a host network and an agent selected from therapeutic, diagnostic, or imaging agents encapsulated therein; delivering the composition to the target biological site; and causing a partial or complete de-crosslinking of the host network resulting in release of the agent therefrom.

In yet another aspect, the invention generally relates to a method for treating or diagnosing a disease or condition. The method includes: administering to a subject in need thereof a therapeutically effective amount of a composition comprising a gel composition of cross-linked hyaluronic acid as a host network and an agent selected from therapeutic, diagnostic, or imaging agents encapsulated therein, optionally with a pharmaceutically acceptable carrier or excipient.

In yet another aspect, the invention generally relates to a method for making a gel. The method includes: (a) reacting hyaluronic acid with a compound having the structure formula V:

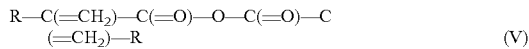   (V)

wherein each R is independently selected from the group consisting of H, $C_1$-$C_{14}$ alkyl group, and halogen; and (b) reacting the product of (a) with a compound having the structural formula:

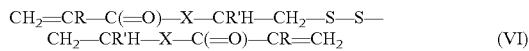   (VI)

wherein each R' is H or —C(=O)O—R", wherein R" is a group comprising a $C_1$-$C_{14}$ alkyl group or a $C_4$-$C_{14}$ aryl moiety; each X is independently selected from NH, O and S.

In yet another aspect, the invention generally relates to a compound having the structural formula:

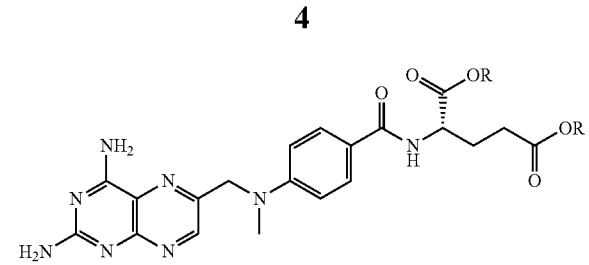

wherein each R is independently selected from the group consisting of aliphatic group and aryl group.

The dye is however stably encapsulated in crosslinked HA-decorated nanoparticles (right). (B) Encapsulation of MMTx within the HA-decorated nanoparticles (slightly colored nature of the solution shows encapsulation). (C) Attempted encapsulation of MTx in HA-decorated nanoparticles (no encapsulation is discernible, attributed to the hydrophilicity of the drug).

Figure 2:
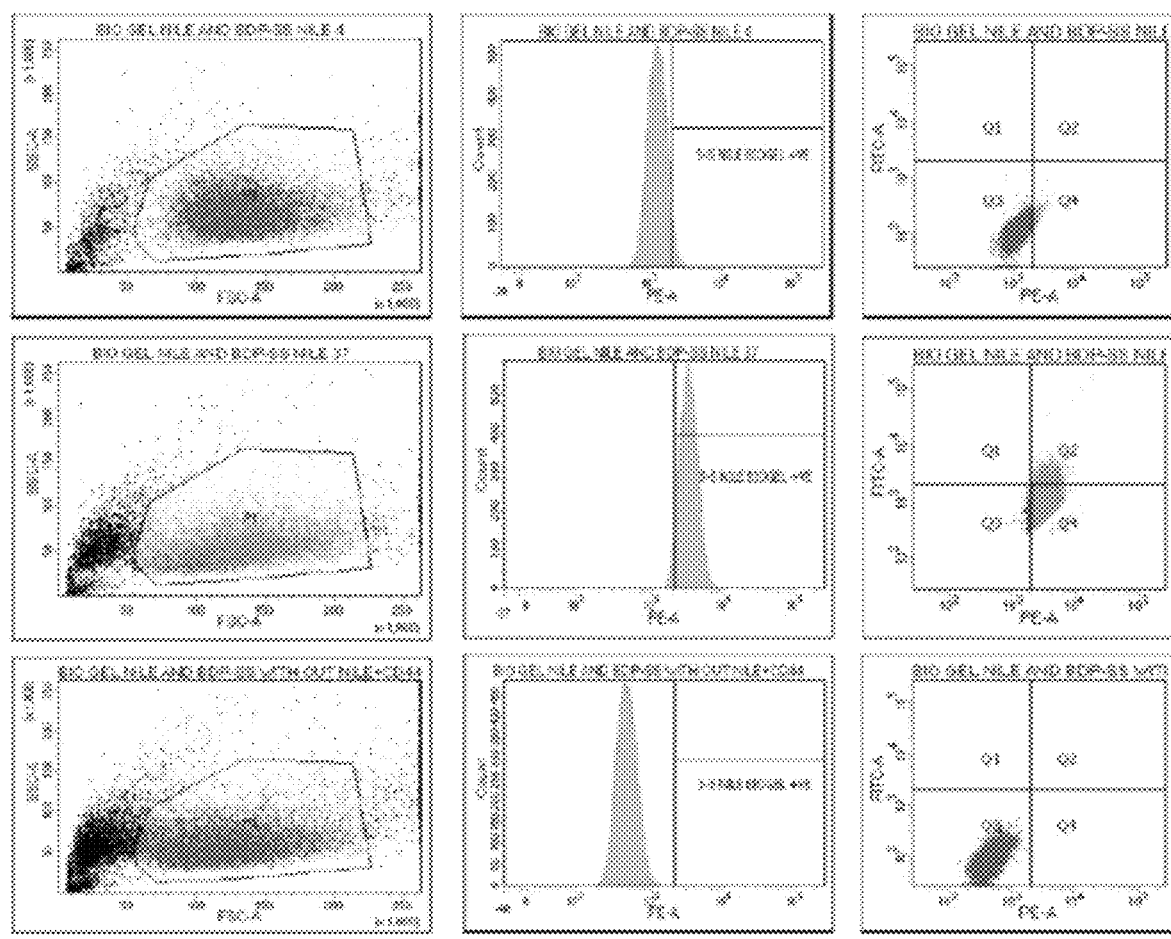
Figure 2:
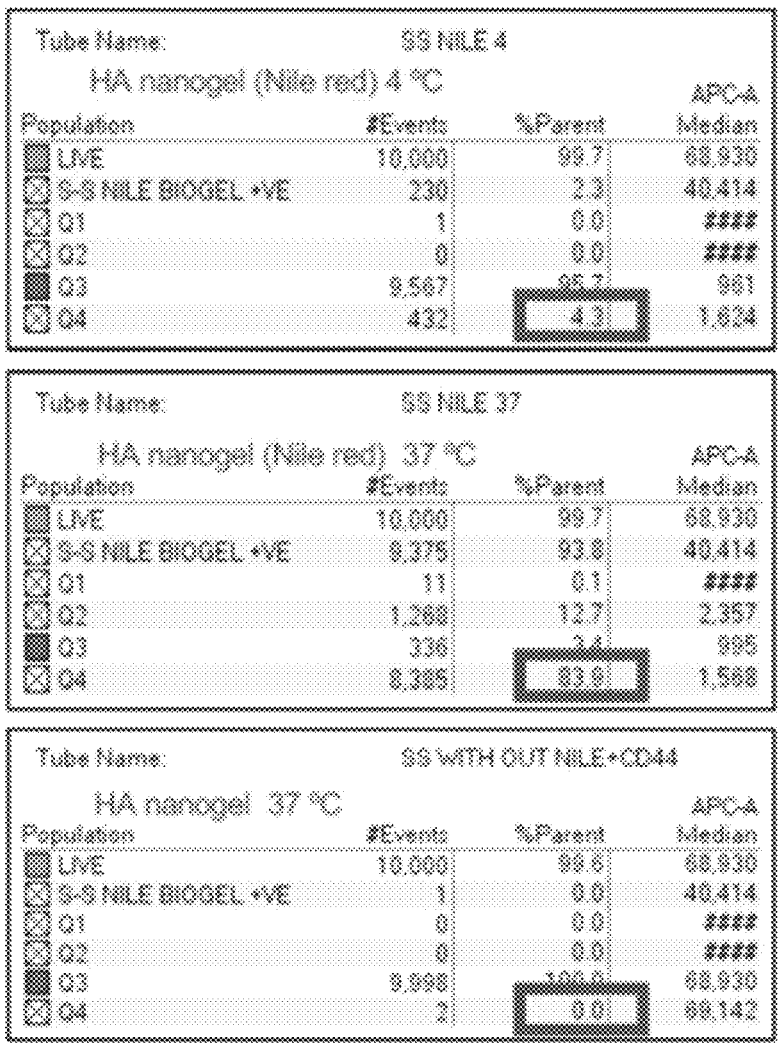
Figure 2:
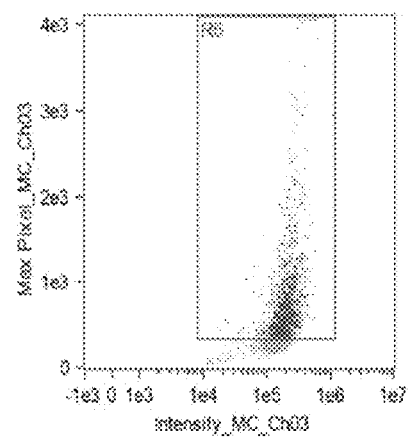
Figure 2:
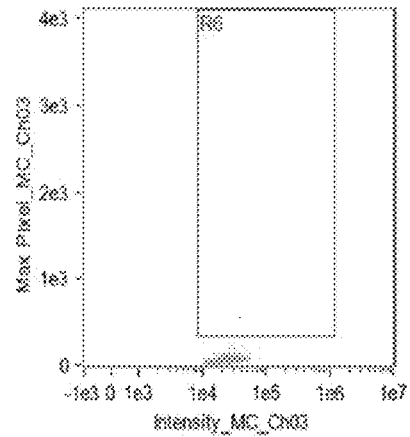

FIG. 2. (A) Cellular uptake results show internalization of HA microgels in cells upon incubation. (B) Effect of HA inhibition on cell uptake with results showing receptor mediated cellular uptake of nanoparticles.

Figure 3:
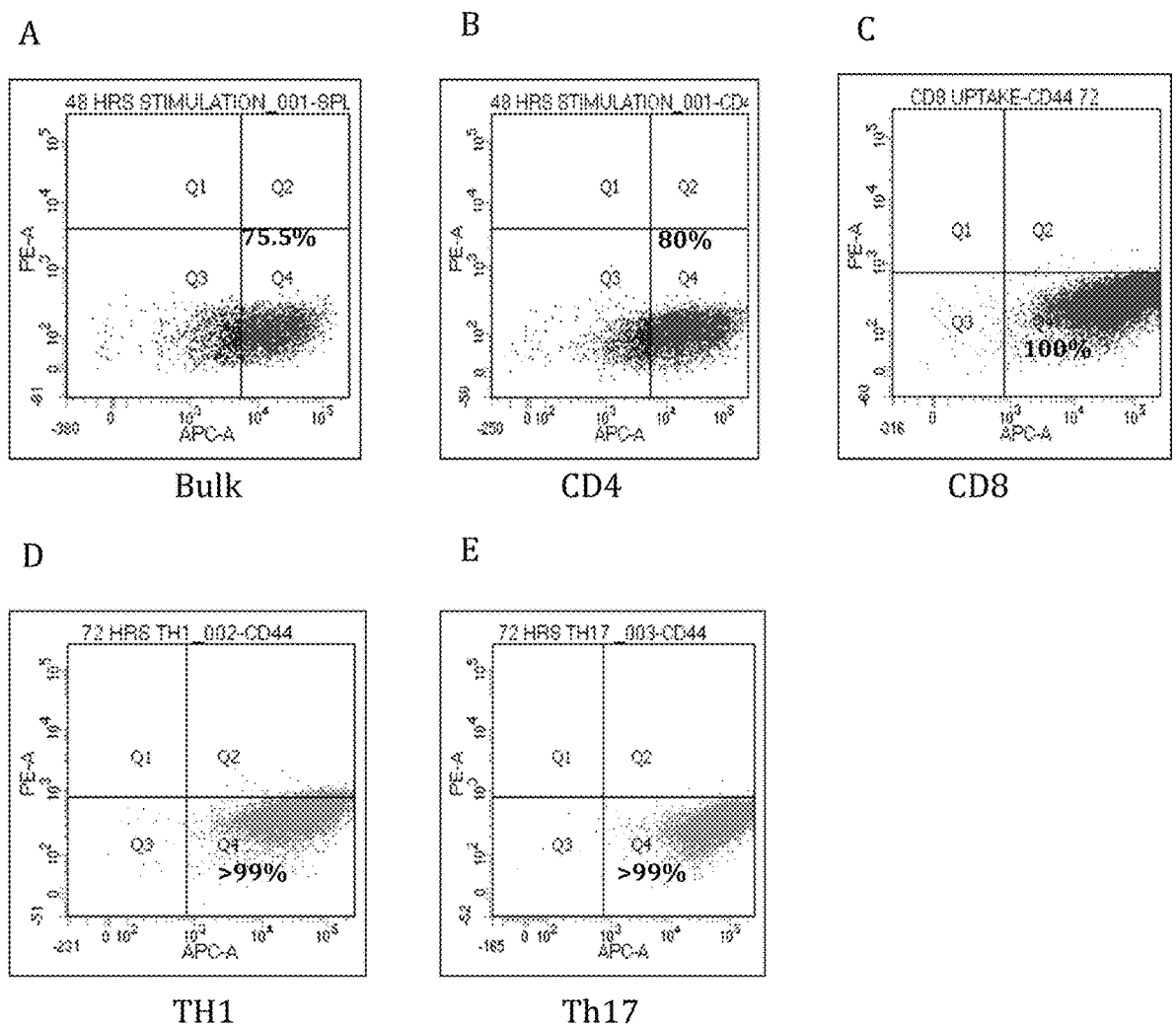

FIG. 3. CD44 expression is increased on activated and differentiated murine T cells.

Figure 4:
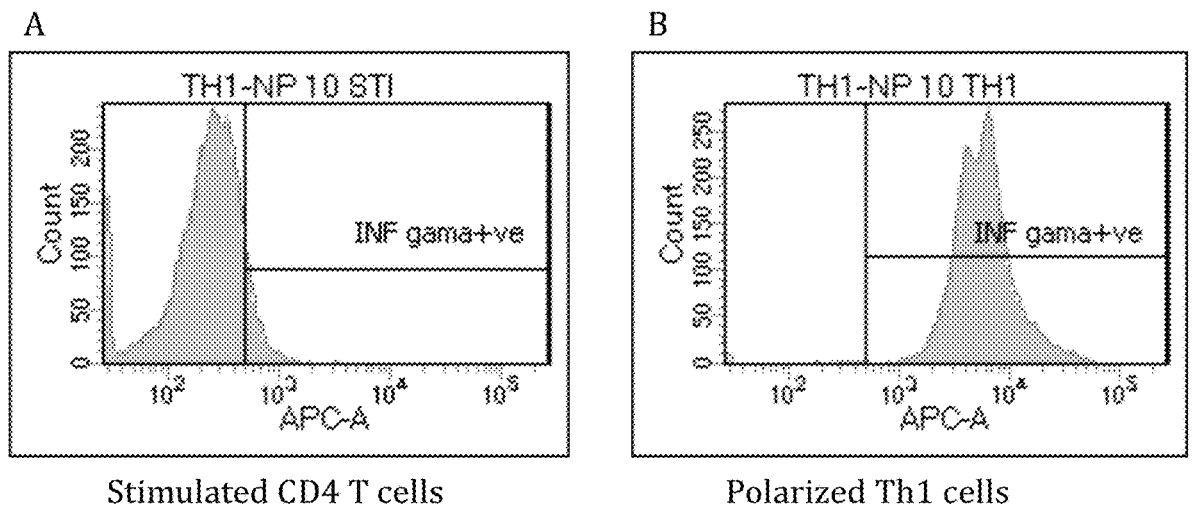

FIG. 4. Baseline expression of the TH1 pro-inflammatory cytokine, interferon gamma (IFNγ) using intracellular staining approaches and flow cytometry.

Figure 5:
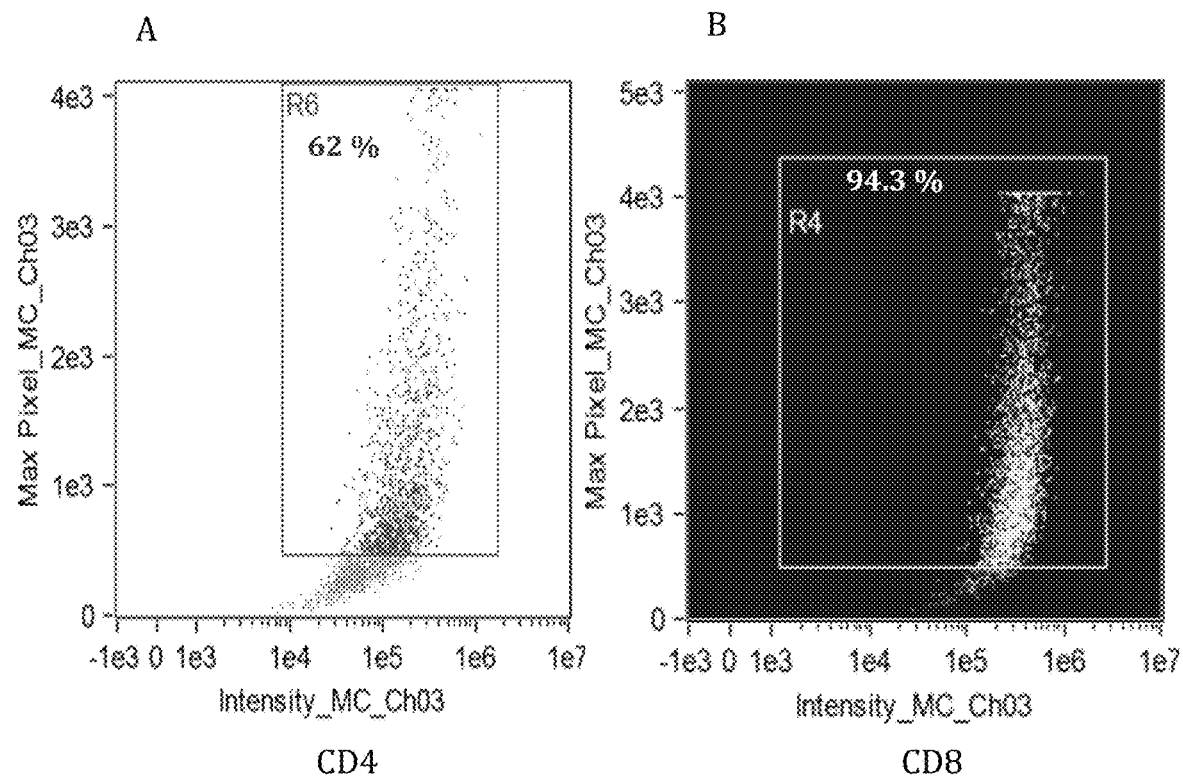

FIG. 5. Nile Red-loaded HA polymeric nanoparticles are internalized by primary murine CD4 and CD8 T cells, as determined by imaging flow cytometry.

Figure 6:
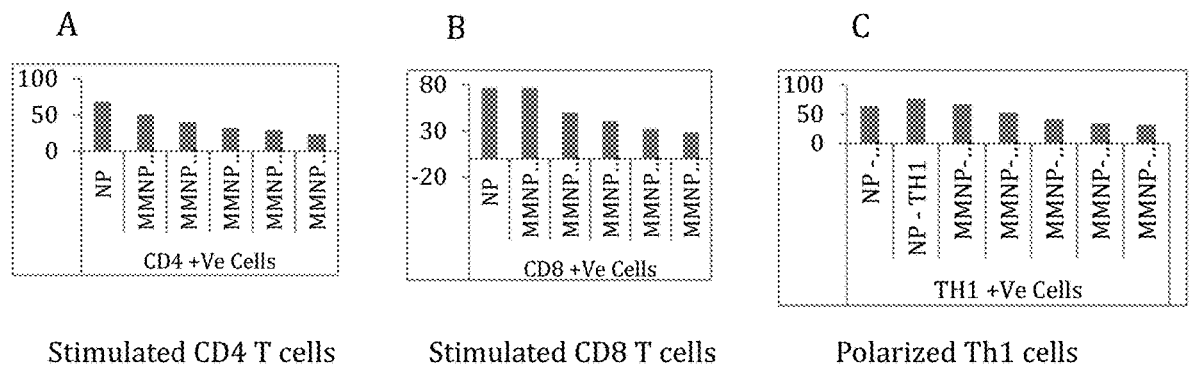

FIG. 6. Modified Methotrexate-loaded HA polymeric nanoparticles cause dose-dependent cytotoxicity in stimulated primary murine CD4 and CD8 T cells, and in CD4 TH1 cells.

Figure 7:
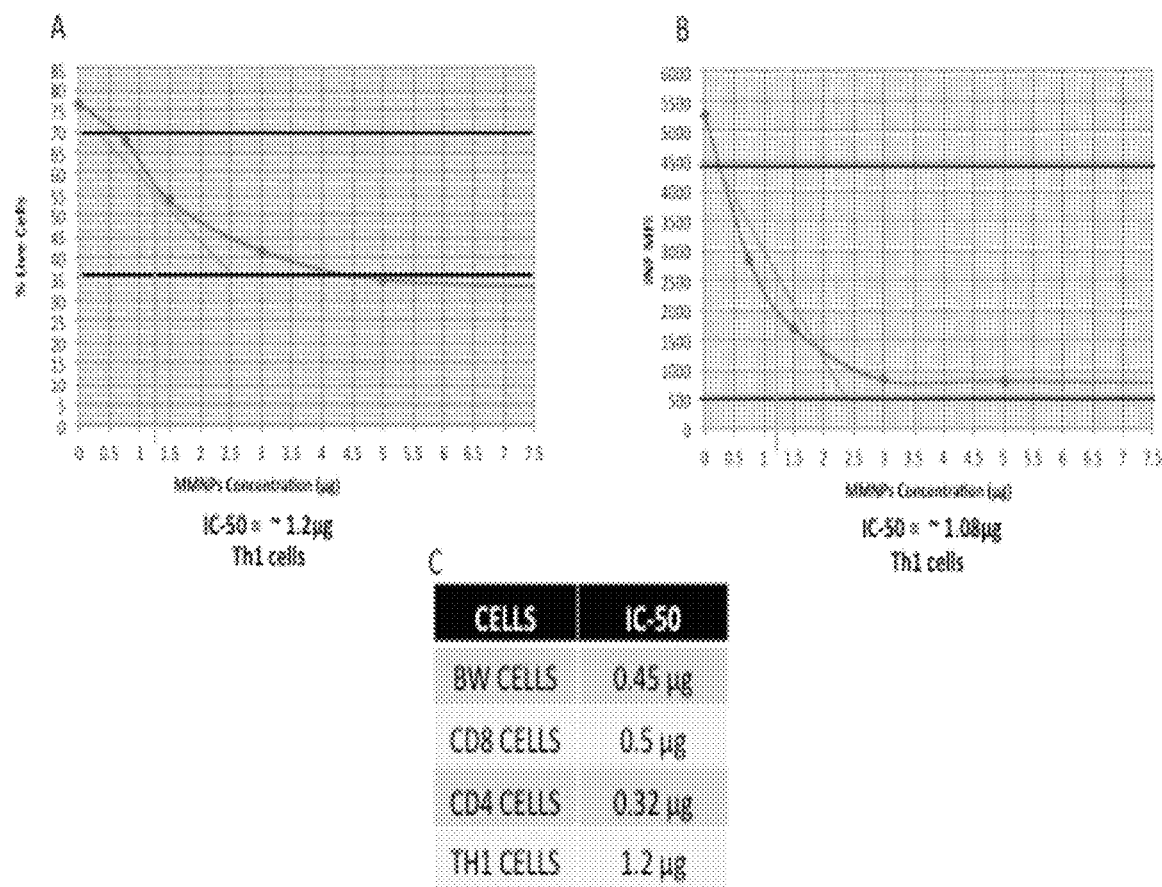

FIG. 7. Calculating the $IC_{50}$ of the modified methotrexate delivered intracellularly by HA polymeric nanoparticles.

Figure 8:
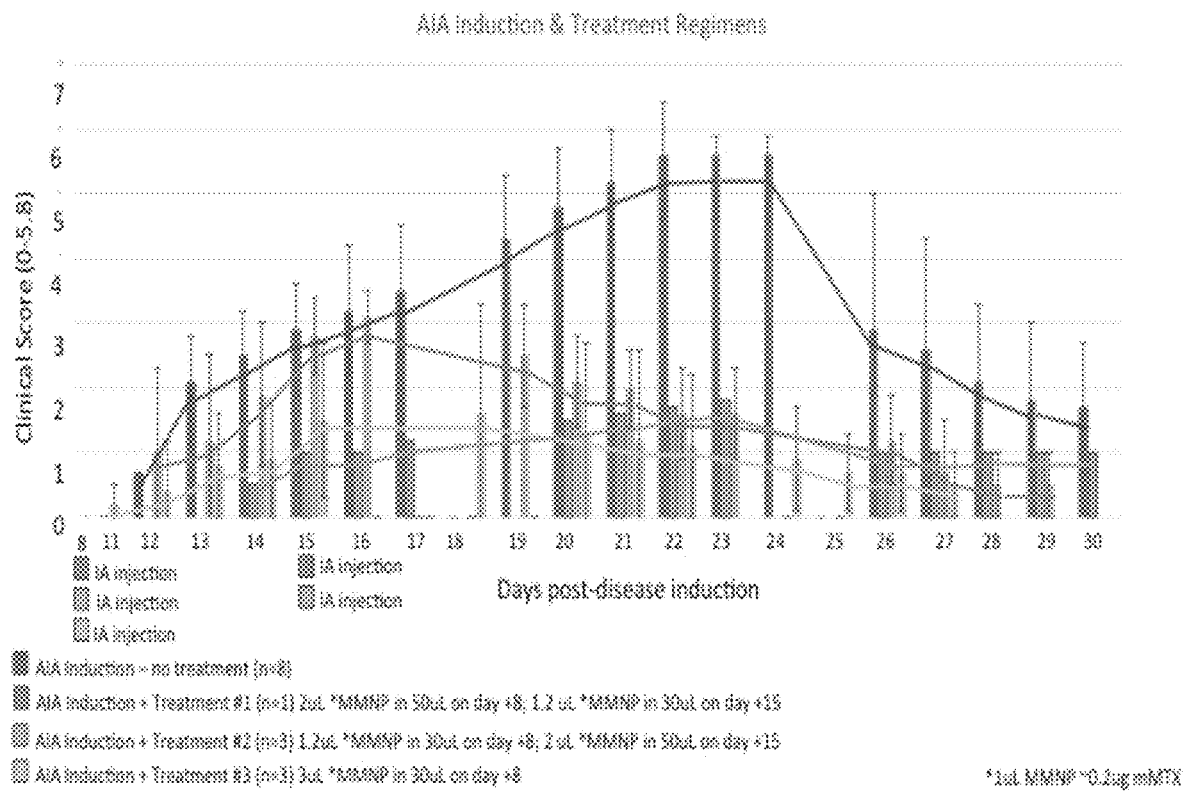

FIG. 8. Intra-articular injection of HA polymeric nanoparticles attenuates disease in a rat model of Adjuvant-Induced Arthritis (AIA).

Figure 9:
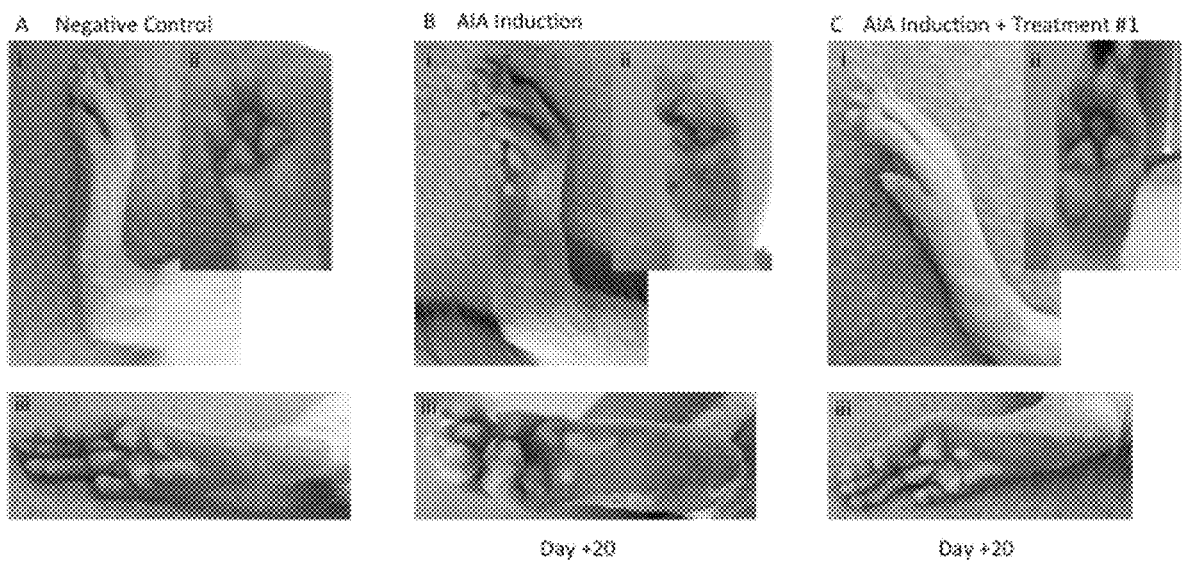

FIG. 9. Intra-articular delivery of mMTX-loaded HA polymeric nanoparticles attenuates swelling in a rat model of AIA.

Figure 10:
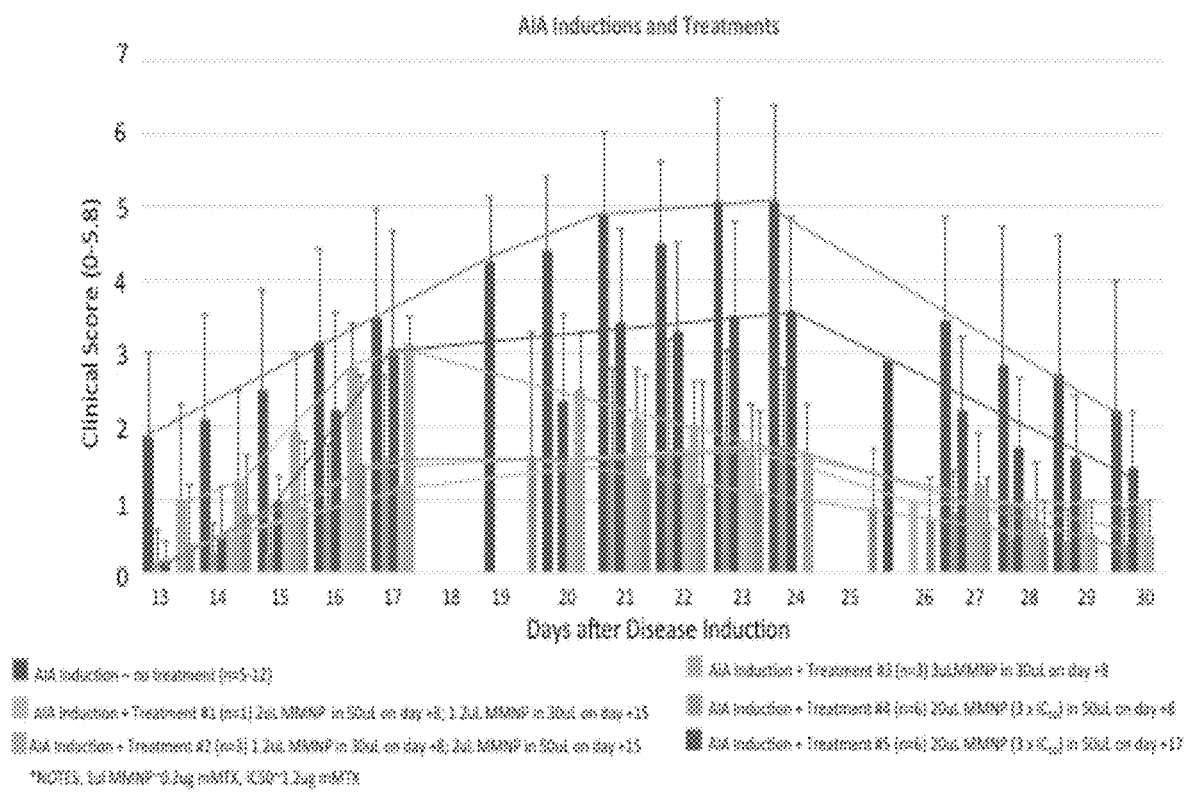

FIG. 10. Expanded in vivo studies show reduced clinical scores following intra-articular injection on day +8 post-disease-induction.

Figure 11:
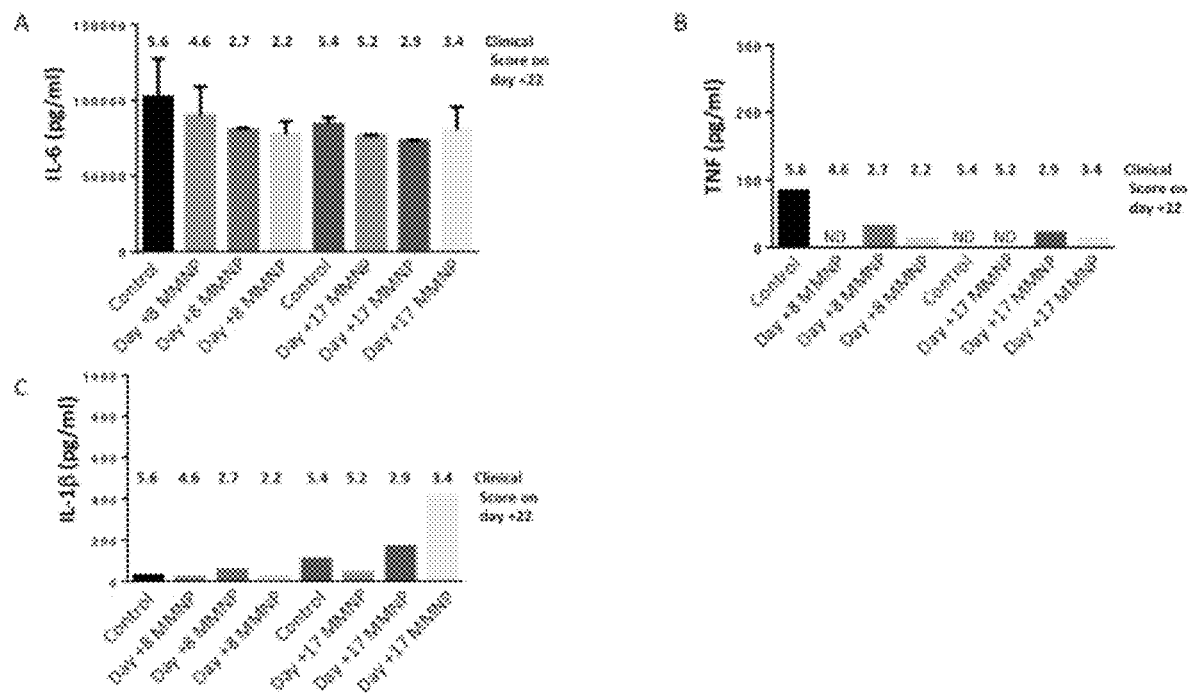

FIG. 11. Plasma cytokine levels on day +22 do not correlate closely with clinical score.

Figure 12:
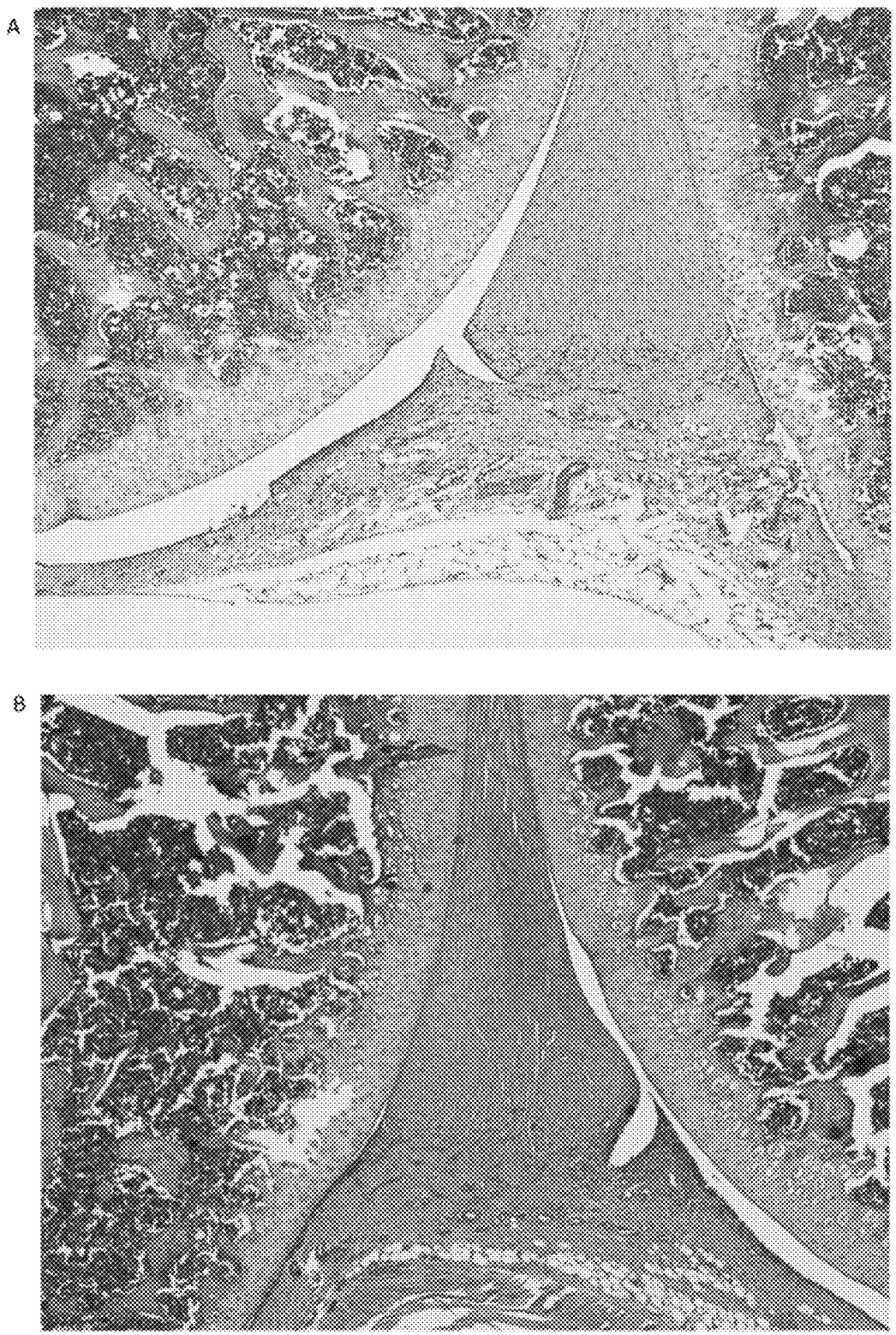
Figure 12:
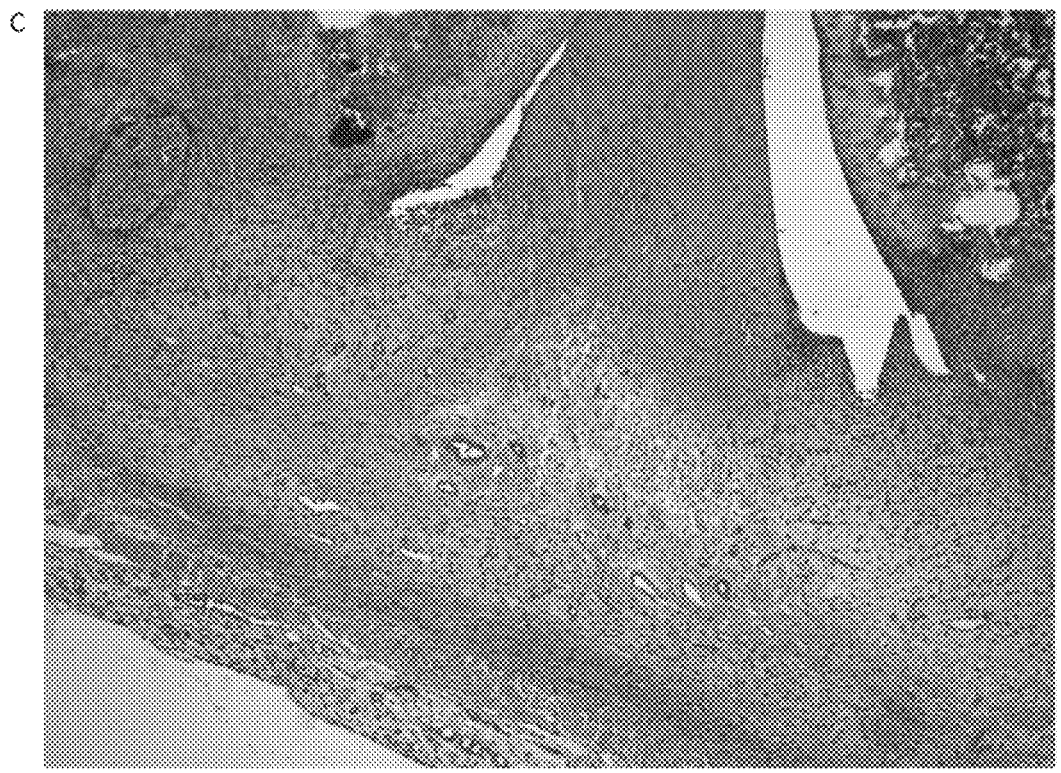
Figure 12:
Figure 12:
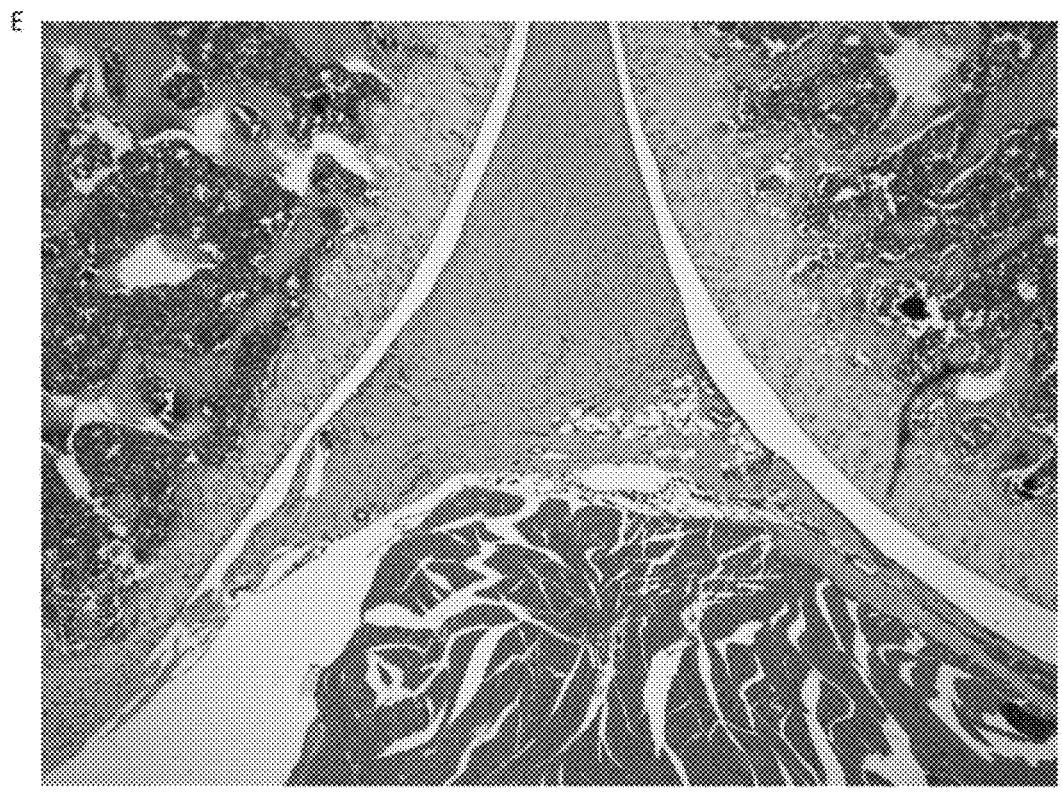
Figure 12:
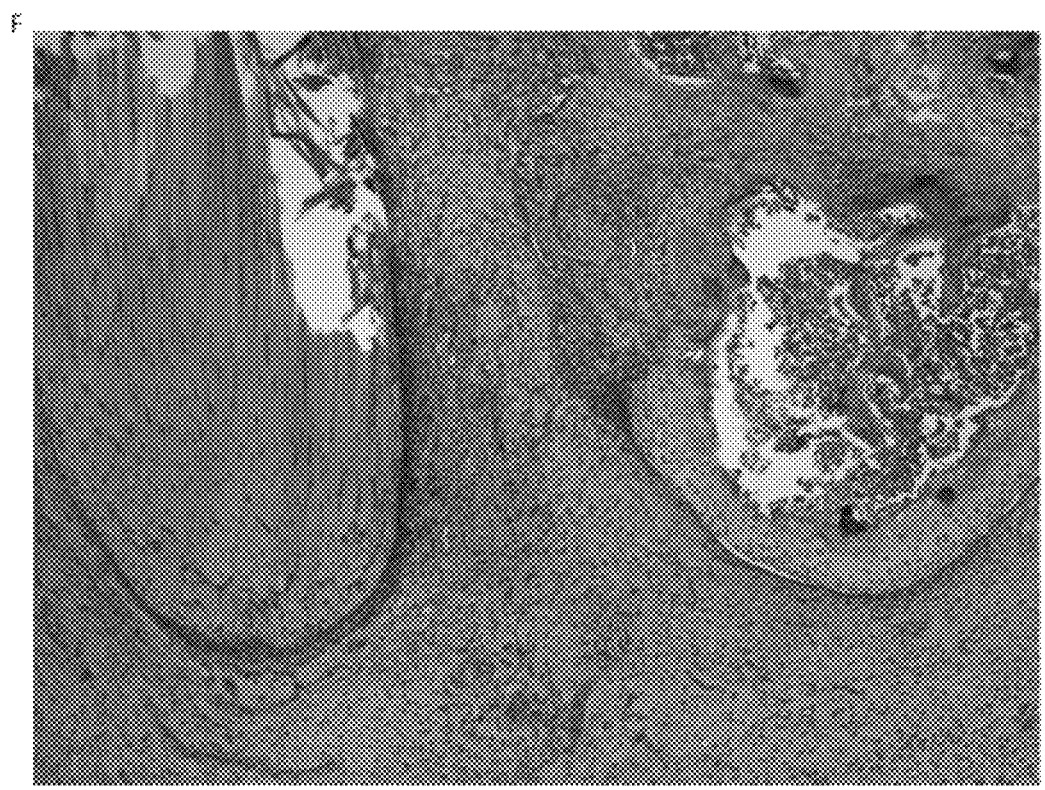
Figure 12:
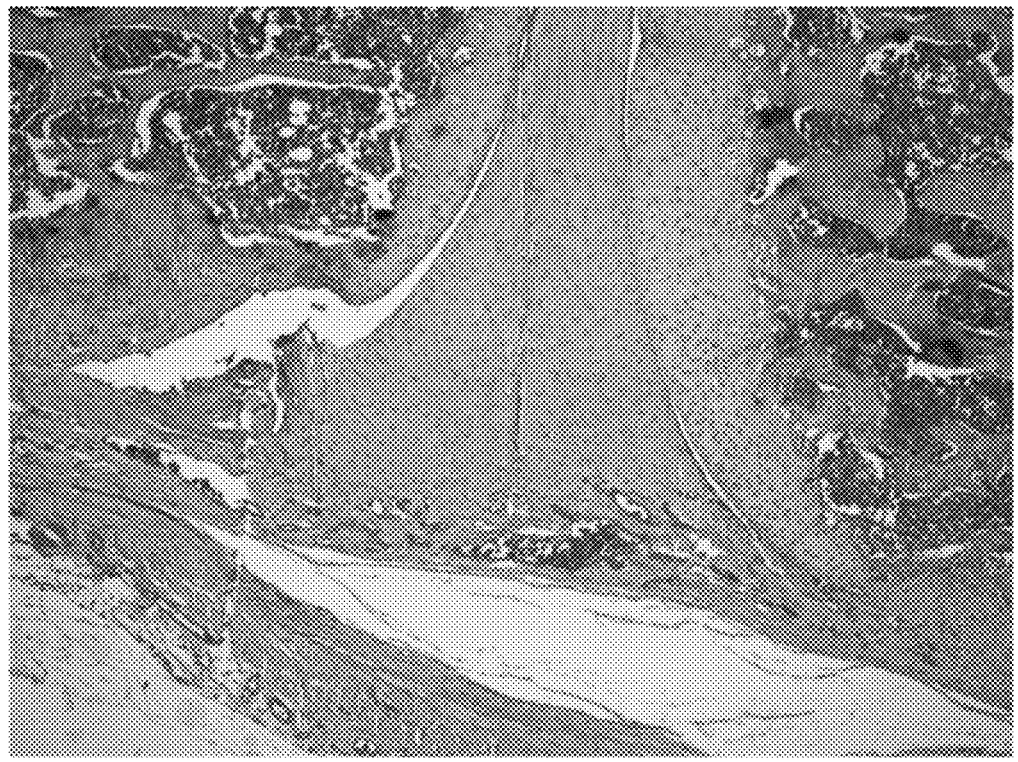
Figure 12:
Figure 12:
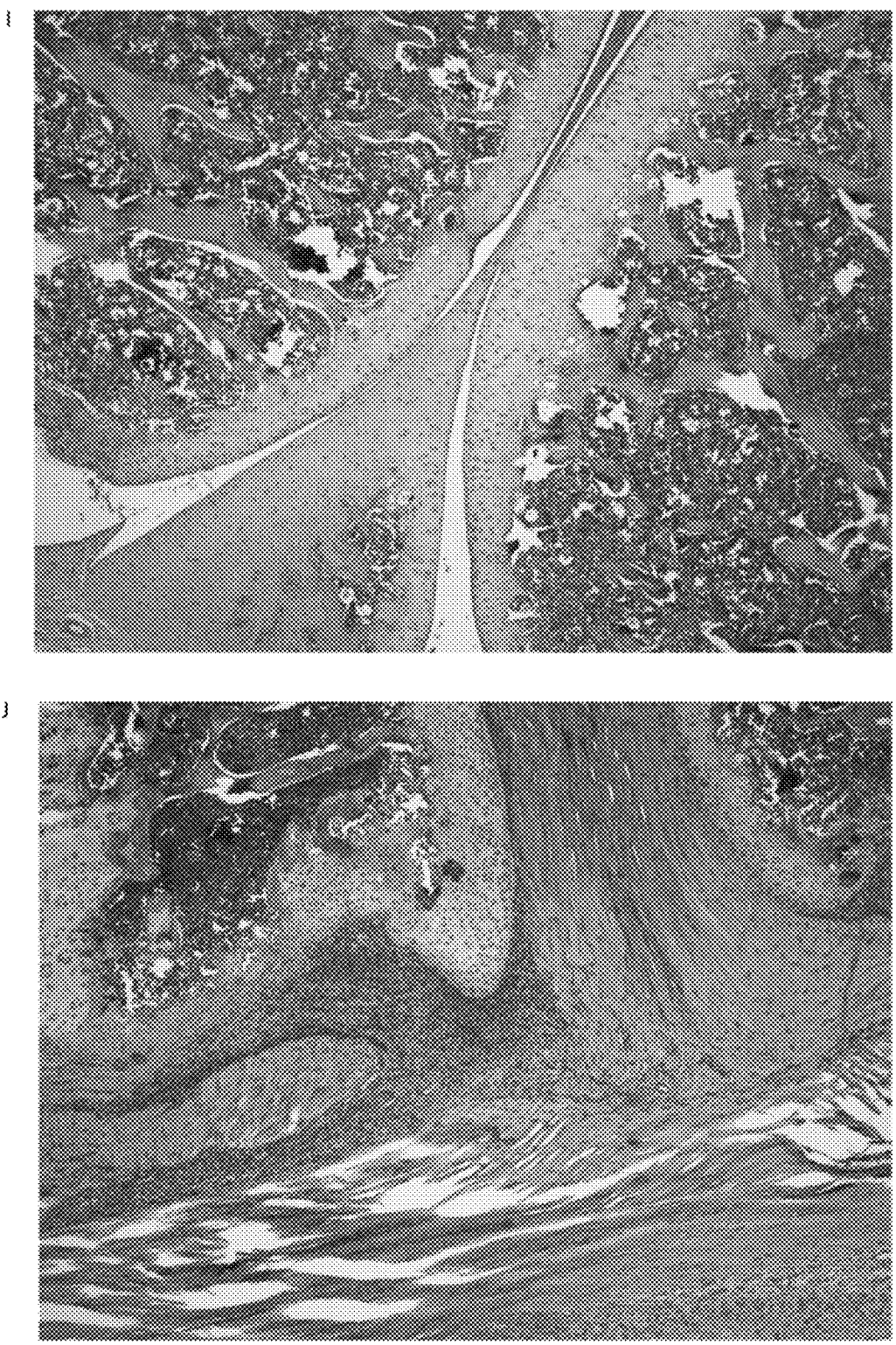
Figure 12:
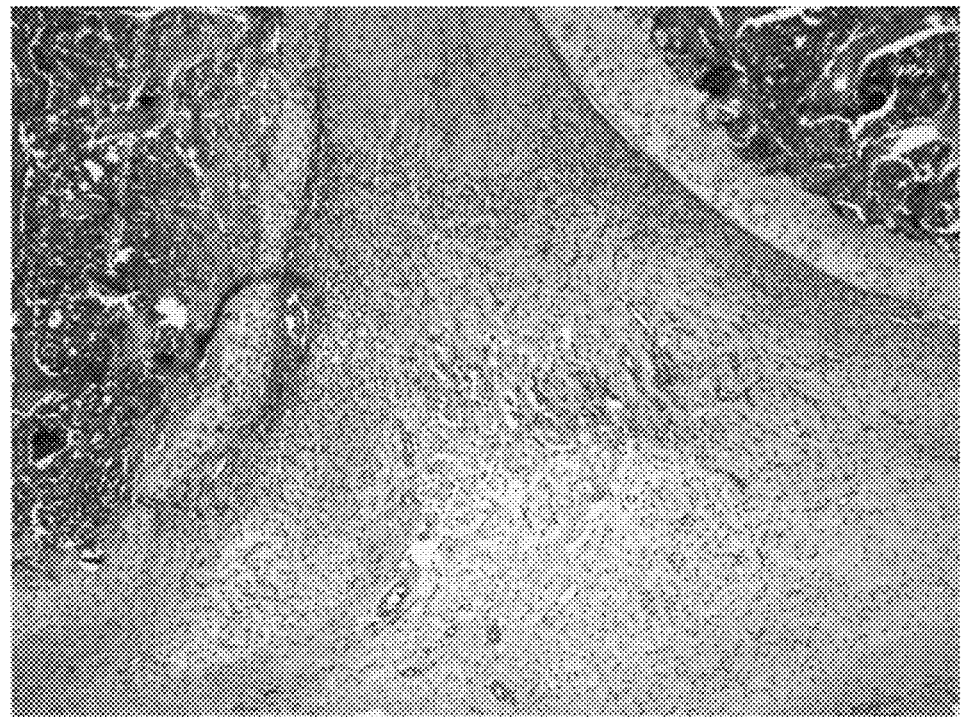
Figure 12:
Figure 12:
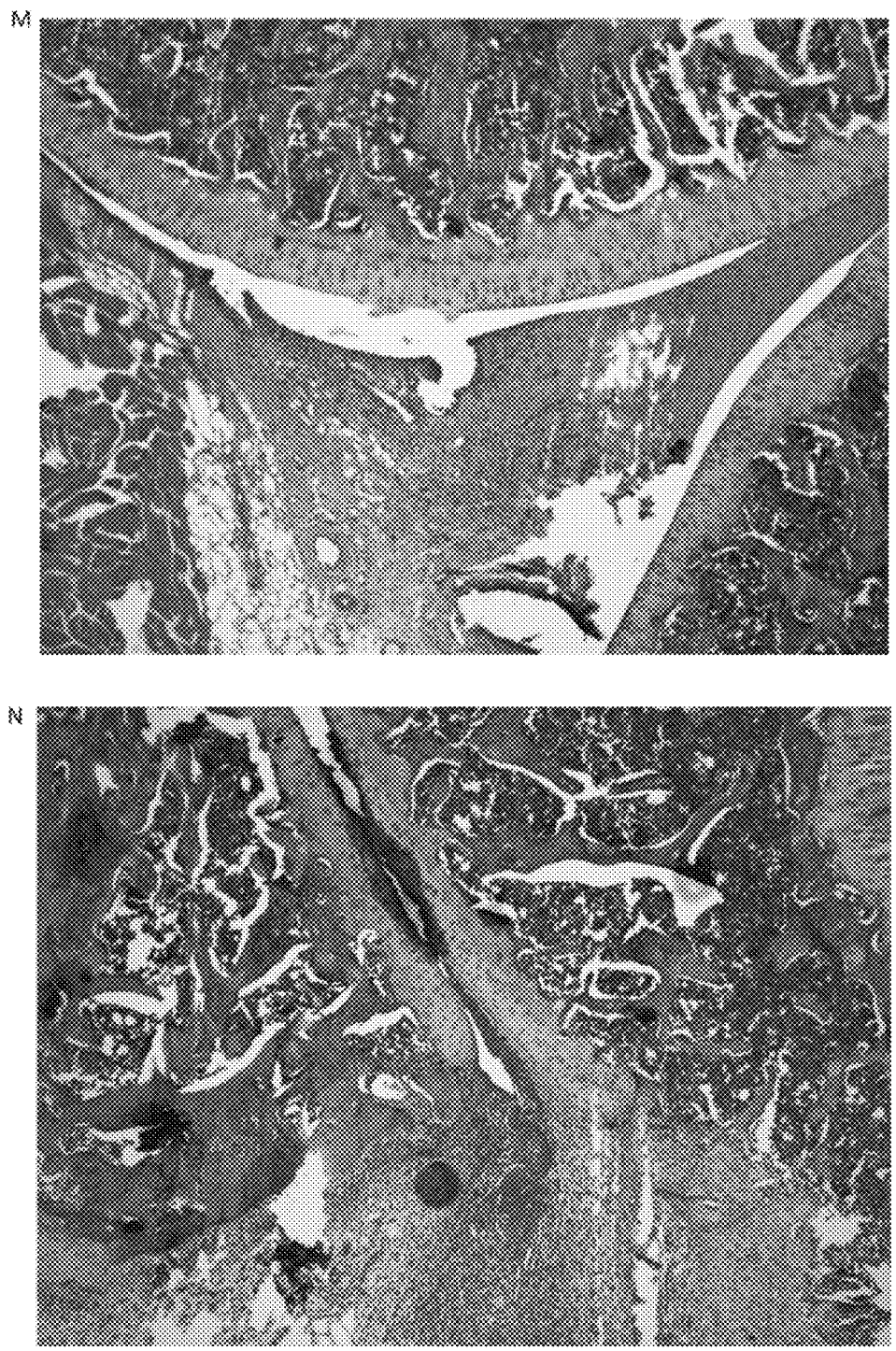

FIG. 12. Histological assessment of localized disease.

Figure 13:
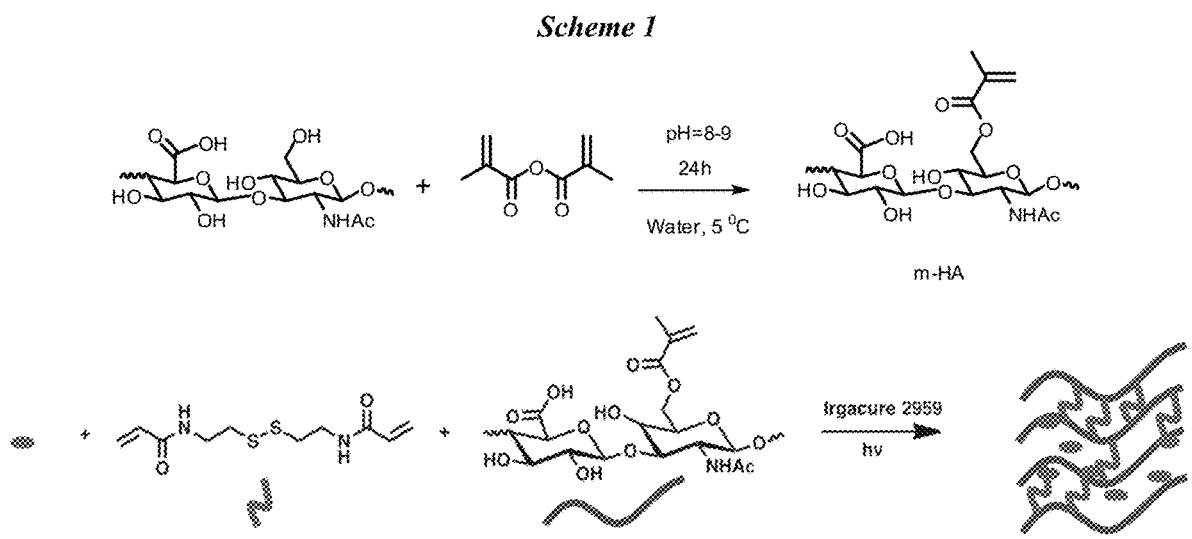

FIG. 13. Synthetic scheme for synthesis of polymer NPs (Scheme 1).

Figure 14:
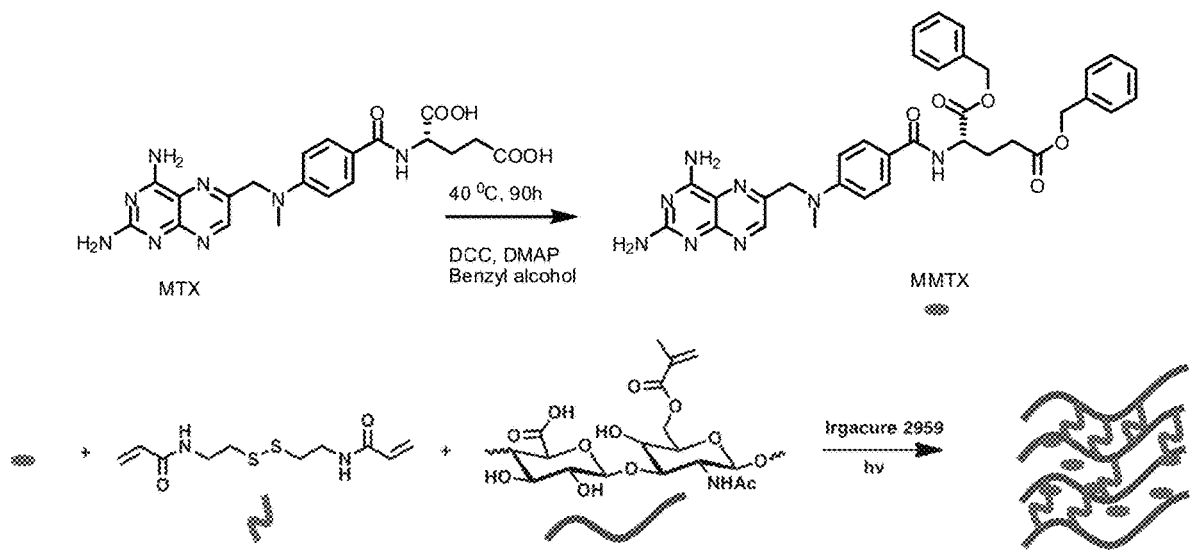

FIG. 14. Synthetic scheme for encapsulation of active drug (Scheme 2).

DEFINITIONS

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example "$C_{1-6}$ alkyl" is intended to encompass, Cl, $C_2$, $C_3$, $C_4$, $C_5$, $C_6$, $C_{1-6}$, $C_1$-5, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "aliphatic" refers to a group or moiety that is not aromatic. An aliphatic group or moiety may be cyclic or non-cyclic, un-saturated or saturated, linear or branched.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —N($R^a$)$_2$, —C(O)$R_a$, —C(O)$OR^a$, —OC(O)N($R^a$)$_2$, —C(O)N($R^a$)$_2$, —N($R^a$)C(O)$OR^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)($OR^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —N($R^a$)$_2$, —C(O)$R_a$, —C(O)$OR^a$, —OC(O)N($R^a$)$_2$, —C(O)N($R^a$)$_2$, —N($R^a$)C(O)$OR^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)($OR^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl) that has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$—OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$N$(R^a)_2$ (where t is 1 or 2), —P(=O)$(R^a)(R^a)$, or —O—P(=O)$(OR^a)_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$N$(R^a)_2$ (where t is 1 or 2), —P(=O)$(R^a)(R^a)$, or —O—P(=O)$(OR^a)_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halogen" refers to fluorine (F), chlorine (Cl), bromine (Br), or iodine (I). As used herein, the term "halide" or "halo", means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroalkyl" refers to an alkyl radical, which have one or more skeletal chain atoms selected from an atom other than carbon, e.g., oxygen, nitrogen, sulfur, phosphorus or combinations thereof. A numerical range can be given, e.g., $C_{1-4}$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH₂CH₂OCH₂OCH₃), (methoxymethoxy) methanyl (—CH₂OCH₂OCH₃) and (methoxyethoxy)methanyl (—CH₂OCH₂CH₂OCH₃) and the like; amines such as (—CH₂CH₂NHCH₃, —CH₂CH₂N(CH₃)₂, —CH₂NHCH₂CH₃, —CH₂N(CH₂CH₃)(CH₃)) and the like.

As used herein, the term "heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 n electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d]pyrimidinyl, 5,6,7,8,9,10-hexahydrocycloocta[d] pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5]thieno [2,3-d]pyrimdinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)₃, —OR$^a$, —SR$^a$, —OC(O)—R$^a$, —N(R$^a$)₂, —C(O)R$_a$, —C(O)OR$^a$, —OC(O)N(R$^a$)₂, —C(O)N(R$^a$)₂, —N(R$^a$)C (O)OR$^a$, —N(R$^a$)C(O)R$^a$, —N(R$^a$)C(O)N(R$^a$)₂, —N(R$^a$)C (NR$^a$)N(R$^a$)₂, —N(R$^a$)S(O)$_t$N(R$^a$)₂ (where t is 1 or 2), —P(=O)(R$^a$)(R$^a$), or —O—P(=O)(OR$^a$)₂ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "hyaluronic acid" or "hyaluronic acids", a.k.a. hyaluronan, hyaluronate, or HA, refer to acidic polysaccharides with different molecular weights constituted by residues of D-glucuronic and N-acetyl-D-glucosamine acids, which occur naturally on certain cell surfaces, in the basic extracellular substances of the connective tissue of vertebrates, in the synovial fluid of the joints, in the endobulbar fluid of the eye, in human umbilical cord tissue and in cocks' combs. Thus, hyaluronic acid generally refers to a whole series of polysaccharides with alternating residues of D-glucuronic and N-acetyl-D-glucosamine acids with varying molecular weights or even the degraded fractions of the same. The terms "hyaluronic acid" and "HA" are used interchangeably herein to refer to an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. These terms also include a salt of HA thereof if not expressly stated otherwise.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the terms "prevent", "preventing", or "prevention" refer to a method for precluding, delaying, averting, or stopping the onset, incidence, severity, or recurrence of a disease or condition. For example, a method is considered to be a prevention if there is a reduction or delay in onset, incidence, severity, or recurrence of a disease or condition or one or more symptoms thereof in a subject susceptible to the disease or condition as compared to a subject not receiving the method. The disclosed method is also considered to be a prevention if there is a reduction or delay in onset, incidence, severity, or recurrence of osteoporosis or one or more symptoms of a disease or condition in a subject susceptible to the disease or condition after receiving the method as compared to the subject's progression prior to receiving treatment. Thus, the reduction or delay in onset, incidence, severity, or recurrence of osteoporosis can be about a 5, 10, 20, 30, 40, 50, 60, 70, 80, 90, 100%, or any amount of reduction in between.

As used herein, a "pharmaceutically acceptable form" of a disclosed compound includes, but is not limited to, pharmaceutically acceptable salts, esters, hydrates, solvates, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof. In some embodiments, a "pharmaceutically acceptable form" includes, but is not limited to, pharmaceutically acceptable isomers and stereoisomers, prodrugs and isotopically labeled derivatives thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchioric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the term "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that is formulated for administration by inhalation will differ from a low dosage of the same agent formulated for oral administration.

As used herein, the term "high dosage" is meant at least 5% (e.g., at least 10%, 20%, 50%, 100%, 200%, or even 300%) more than the highest standard recommended dosage of a particular compound for treatment of any human disease or condition.

As used herein, the term "prodrug" (or "pro-drug") refers to a pharmacological derivative of a parent drug molecule that requires biotransformation, either spontaneous or enzymatic, within the organism to release the active drug. Such prodrugs are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form.

Prodrug forms often offer advantages of solubility, tissue compatibility, or delayed release in the mammalian organism. (See, Bundgard, Design of Prodrugs, pp. 7-9,21-24, Elsevier, Amsterdam 1985 and Silverman, The Organic Chemistry of Drug Design and Drug Action, pp. 352-401, Academic Press, San Diego, Calif., 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substituents disclosed herein.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^1H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. (See, WO 2007/005643, WO 2007/005644, WO 2007/016361, and WO 2007/016431.)

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

DETAILED DESCRIPTION OF THE INVENTION

The invention is based in part on the unexpected discovery of a novel class of crosslinked nanoparticles, based on hyaluronic acid (HA) polymer and crosslinked with appropriate reversible crosslinkers, which can be used to encapsulate therapeutic agents or other payloads. These nanoparticles target specific cell types in controllable delivery and release.

Thus, the invention provides a platform methodology for targeted delivery of a payload (e.g., therapeutic, diagnostic or imaging agents) to a desired site and for controlled release of the payload at the desired site triggered by the local environment that causes partial or complete decrosslinking of the nanoparticles (e.g., reversible crosslinking and encapsulation with delivery and release at a biological site in response to a local redox- or pH stimuli).

The invention additionally provides novel methods of preparation and use of the HA-based nanoparticles disclosed herein.

CD44 is a cell-adhesion molecule that is ubiquitously expressed on leukocytes and parenchymal cells. It has been implicated, together with its ligand hyaluronic acid (HA), in several inflammatory diseases. The CD44 antigen is a cell-surface glycoprotein involved in cell-cell interactions, cell adhesion and migration. In humans, the CD44 antigen is encoded by the CD44 gene on Chromosome 11. CD44 participates in a wide variety of cellular functions including lymphocyte activation, recirculation and homing, hematopoiesis, and tumor metastasis. CD44 can interact with other ligands, such as osteopontin, collagens, and matrix metalloproteinases (MMPs). CD44 function is controlled by its posttranslational modifications. Under inflammatory conditions, CD44 on endothelial cells presents hyaluronan to CD44 on activated T lymphocytes and mediates a rolling interaction under flow conditions.

CD44 is highly expressed on memory effector T cells, and has been shown to mediate the recruitment of activated cells into the synovium of affected joints in animal models of Rheumatoid Arthritis. Furthermore, studies show that administering CD44-neutralizing antibodies can reduce disease severity in animal models of Rheumatoid Arthritis. CD44 is also frequently highly expressed in many cancers including breast, prostate, and renal cancers, non-Hodgkin lymphoma and some leukemias.

In one aspect, the invention generally relates to a gel composition comprising cross-linked hyaluronic acid, wherein the hyaluronic acid is cross-linked by one or more cross-linking groups that comprises structural formula I:

—C(=O)—CR(R$^1$)—CH$_2$—CR(R$^2$)—C(=O)—     (I)

and one or more cross-linking groups that comprises structural formula II:

—CH$_2$—S—S—CH$_2$—     (II)

wherein each of R, R$^1$ and R$^2$ is independently selected from the group consisting of H, a C$_1$-C$_{14}$ alkyl group, a C$_4$-C$_{14}$ aryl group, a halogen, or a bond linking the cross-linking group to the crosslinked hyaluronic acid network.

In certain embodiments of the gel composition, the hyaluronic acid is cross-linked by one or more cross-linking groups that comprises structural formula Ia:

—C(=O)—CRH—CH$_2$—CRH—C(=O)—     (Ia)

In certain embodiments of the gel composition, the one or more cross-linking groups that comprises structural formula II comprises formula III:

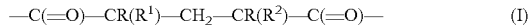
(III)

wherein each R' is H, —C(=O)O—R", or —C(=O)—NH—R", wherein R" is a group comprising a C$_1$Cl$_4$ alkyl group or a C$_4$-C$_{14}$ aryl moiety; and each X is independently selected from NH, O and S.

In certain embodiments, the one or more cross-linking groups that comprises structural formula III comprises formula IV:

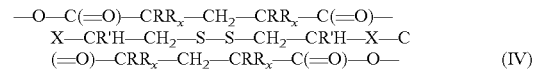
(IV)

wherein each R$_x$ independently represents a bond linking the cross-linking group to the crosslinked hyaluronic acid network; each X is independently selected from NH, O and S.

In certain embodiments, at least one X is NH. In certain embodiments, each X is NH.

In certain embodiments, at least one X is O or S. In certain embodiments, each X is O or S.

In certain embodiments, each X is O. In certain embodiments, each X is S.

In certain embodiments, one X is NH and the other X is O. In certain embodiments, one X is NH and the other X is O.

The Rs may be identical or different. In certain embodiments, each R is H. In certain embodiments, each R is independently a C$_1$-C$_{14}$ alkyl group. In certain embodiments, each R is independently a C$_1$-C$_6$ alkyl group. In certain embodiments, R is independently a C$_1$-C$_3$ alkyl group. In certain embodiments, R is independently a C$_4$-C$_6$ alkyl group. In certain embodiments, the Rs are identical. In certain embodiments, the Rs are different.

The R's may be identical or different. In certain embodiments, each R' is H. In certain embodiments, each R' is independently selected from the group consisting of —C(=O)O—R" and —C(=O)—NH—R". In certain embodiments, each R' is —C(=O)O—R". In certain embodiments, each R' is —C(=O)—NH—R". In certain embodiments, one R' is —C(=O)O—R" and one R' is —C(=O)—NH—R". In certain embodiments, the R's are identical. In certain embodiments, the R's are different.

In certain embodiments, R" is a C$_1$-C$_{14}$ alkyl group. In certain embodiments, R" is a C$_1$-C$_6$ alkyl group. In certain embodiments, R" is independently a C$_1$-C$_3$ alkyl group. In certain embodiments, R is independently a C$_4$-C$_6$ alkyl group. In certain embodiments, the R"s are identical. In certain embodiments, the R"s are different.

In certain embodiments, R" is a C$_4$-C$_{14}$ aryl moiety. In certain embodiments, R" is independently a C$_4$-C$_6$ aryl moiety. In certain embodiments, R is independently a C$_5$-C$_{10}$ aryl moiety. In certain embodiments, the R"s are identical. In certain embodiments, the R"s are different.

R$_x$ may be any suitable bond providing linkage from the cross-linking group to the crosslinked hyaluronic acid network. In certain embodiments, the bond is a single bond, for example, a C—C single bond, a C-heteroatom single bond (e.g., C—O, C—S, C—N), a C=C double bond, or a C=N double bond.

Depending on the application for the gel composition, the degree of crosslinking may vary. In certain embodiments, the cross-linked hyaluronic acid has a degree of cross-linking from about 1% to about 100% (e.g., from about 1% to about 99%, from about 1% to about 90%, from about 1% to about 80%, from about 1% to about 70%, from about 1% to about 50%, from about 1% to about 30%, from about 1% to about 20%, from about 1% to about 10%, from about 5% to about 100%, from about 10% to about 100%, from about 20% to about 100%, from about 30% to about 100%, from about 50% to about 100%, from about 60% to about 100%, from about 80% to about 100%, from about 95% to about 100%, from about 25% to about 99%, from about 5% to about 50%, from about 10% to about 50%, from about 20% to about 50%, from about 50% to about 99%, from about 50% to about 70%, from about 70% to about 99%, from about 85% to about 99%).

Depending on the application for the gel composition, the molecular weight of the gel composition may vary. In certain embodiments, the starting hyaluronic acid, prior to cross-linking, has a molecular weight from about 1,000 to about 5,000,000 (e.g., from about 5,000 to about 5,000,000, from about 10,000 to about 5,000,000, from about 50,000 to about 5,000,000, from about 100,000 to about 5,000,000, from about 250,000 to about 5,000,000, from about 500,000 to about 5,000,000, from about 1,000,000 to about 5,000,000, from about 2,000,000 to about 5,000,000, from about 1,000 to about 2,000,000, from about 1,000 to about 1,000,000, from about 1,000 to about 500,000, from about 1,000 to about 200,000, from about 1,000 to about 100,000, from about 1,000 to about 50,000, from about 1,000 to about 20,000, from about 1,000 to about 10,000, from about 5,000 to about 2,000,000, from about 20,000 to about 2,000,000, from about 50,000 to about 2,000,000, from about 100,000 to about 2,000,000, from about 500,000 to about 2,000,000).

The ratios of the different crosslinking groups may be adjusted as appropriate based on the application at hand. In certain embodiments, the ratio of the cross-linking group (I) to the cross-linking (II) is from about 1:10 to about 10:1 (e.g., from about 1:5 to about 5:1, from about 1:4 to about 4:1, from about 1:3 to about 3:1, from about 1:2 to about 2:1, from about 1:1.5 to about 1.5:1, from about 1:1.2 to about 1.2:1, from about 1:1.1 to about 1.1:1, about 1:1).

In another aspect, the invention generally relates to a composition comprising a gel composition of cross-linked hyaluronic acid disclosed herein as a host network and an agent selected from therapeutic, diagnostic, or imaging agents encapsulated therein.

In certain embodiments of the composition, the agent is non-covalently encapsulated in the host network.

In certain embodiments of the composition, the agent is releasable upon partial or complete de-crosslinking of the host network.

In certain embodiments of the composition, the agent is releasable upon partial or complete de-crosslinking of the host network when delivered to a biological site.

In certain embodiments of the composition, the agent is releasable upon partial (e.g., about 20%, about 30%, about 40%, about 50%, about 70%, about 80%, about 90%) de-crosslinking of the host network. In certain embodiments of the composition, the agent is releasable upon complete (e.g., >about 95%, >about 98%, >about 99%, about 100%) de-crosslinking of the host network.

In certain embodiments of the composition, from about 1% to about 100% (e.g., from about 10% to about 100%, from about 20% to about 100%, from about 30% to about 100%, from about 40% to about 100%, from about 50% to about 100%, from about 70% to about 100%, from about 90% to about 100%) of the encapsulated agent is released at the biological site.

In certain embodiments, the release of the payload at a biological site is triggered by local redox stimuli.

In certain embodiments, the release of the payload at a biological site is triggered by local pH stimuli.

The agent may be any suitable agent (e.g., therapeutic, diagnostic, imaging agents). In certain embodiments of the composition, the agent is a therapeutic agent. In certain embodiments of the composition, the agent is a diagnostic agent. In certain embodiments of the composition, the agent is an imaging agent. In certain embodiments, more than one agent (e.g., two different agents are encapsulated) is encapsulated.

In certain embodiments, the therapeutic agent is an immune system modulator.

The terms "immune system modulator" or "immunomodulator" refer to an agent that when present, alters, suppresses or stimulates the body's immune system. Typically, an immunomodulator of use stimulates immune cells to proliferate or become activated in an immune response cascade, such as macrophages, dendritic cells, B-cells, and/or T-cells. In some cases, an immunomodulator may suppress proliferation or activation of immune cells.

In certain embodiments, the therapeutic agent is a chemotherapy agent or chemotherapeutic agent.

The terms "chemotherapy" or "chemotherapeutic" agent refer to an agent (e.g., a small molecule chemical compound) useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SUI 1248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin I and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33: 183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esonibicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, 111.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

In certain embodiments, the therapeutic agent is a derivative of methotrexate.

In certain embodiments, the therapeutic agent is an ester of methotrexate. In certain embodiments, the therapeutic agent is an aryl ester of methotrexate.

In certain embodiments, the therapeutic agent is a di-ester of methotrexate. In certain embodiments, the therapeutic agent is a bis-aryl ester of methotrexate.

In yet another aspect, the invention generally relates to a pharmaceutical composition comprising a di-ester of methotrexate.

Any suitable di-ester of methotrexate may be employed, for example, compounds of the structural formula:

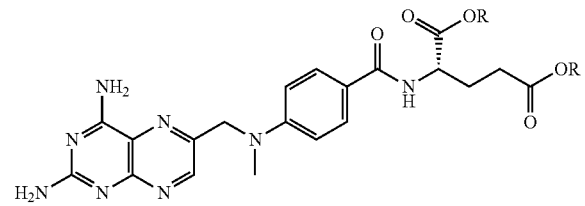

wherein each R is independently selected from the group consisting of aliphatic groups and aryl groups.

In certain embodiments, at least one R is an aliphatic group.
In certain embodiments, each R is an aliphatic group.
In certain embodiments, at least one R is an aryl group.
In certain embodiments, each R is an aryl group.
In certain embodiments, each R is a benzyl group.
In certain embodiments, one R is an aliphatic group and one R is an aryl group.

In certain embodiments, R's are chosen such that upon hydrolysis byproduct(s) that are generally regarded as safe (GRAS) are produced. For example, when R is a benzyl group, the hydrolyzed product, benzyl alcohol is a GRAS molecule.

In certain embodiments, R's are chosen such that a desired encapsulation profile is achieved for a given application. Without wishing to be bound by the theory, the hydrophilicity of a di-ester of methotrexate can influence its encapsulation in a host network.

In certain embodiments, the di-ester of methotrexate is characterized by a log P (log of the octanol/water partition coefficient; see, e.g., Bombuwala et. al., *Beilstein J. Org. Chem.* 2006, 2:13) in the range from about 1.5 to about 10 (e.g., from about 1.5 to about 10, from about 2.0 to about 10, from about 2.5 to about 10, from about 2.0 to about 10, from about 3.5 to about 10, from about 4.0 to about 10, from about 4.5 to about 10, from about 5.0 to about 10, from about 6.0 to about 10, from about 7.0 to about 10, from about 8.0 to about 10, from about 1.5 to about 4.0, from about 4.0 to about 9.0, from about 5.0 to about 9.0, from about 6.0 to about 9.0).

In certain embodiments, the di-ester of methotrexate is encapsulated in a network of cross-linked hyaluronic acid. In certain embodiments, more than one (e.g., two different) di-esters of methotrexate is encapsulated in a network of cross-linked hyaluronic acid.

In certain embodiments, the encapsulated payload(s) are preferably 100% retained prior to the desired release at the target biological site. In certain embodiments, the encapsulated payload(s) are about 80% or greater retained prior to the desired release at the target biological site.

In certain embodiments, the encapsulated payload(s) are about 85% or greater retained prior to the desired release at the target biological site. In certain embodiments, the encapsulated payload(s) are about 90% or greater retained prior to the desired release at the target biological site. In certain embodiments, the encapsulated payload(s) are about 95% or greater retained prior to the desired release at the target biological site. In certain embodiments, the encapsulated payload(s) are about 98% or greater retained prior to the desired release at the target biological site. In certain embodiments, the encapsulated payload(s) are about 99% or greater retained prior to the desired release at the target biological site. In certain embodiments, the encapsulated payload(s) are about 99.5% or greater retained prior to the desired release at the target biological site. In certain embodiments, the encapsulated payload(s) are about 99.9% or greater retained prior to the desired release at the target biological site.

In certain embodiments, the di-ester of methotrexate is releasable upon partial or complete de-crosslinking of the network of cross-linked hyaluronic acid when delivered to a biological site.

In certain embodiments, from about 1% to about 100% (e.g., from about 10% to about 100%, from about 20% to about 100%, from about 30% to about 100%, from about 40% to about 100%, from about 50% to about 100%, from about 70% to about 100%, from about 90% to about 100%) of the di-ester of methotrexate is released at the biological site.

In certain embodiments, the gel compositions or pharmaceutical compositions are present in the form of nanoparticles. In certain embodiments, the nanoparticles are characterized by having a size from about 10 nm to about 1000 nm (e.g., from about 10 nm to about 500 nm, from about 10 nm to about 200 nm, from about 10 nm to about 100 nm, from about 10 nm to about 50 nm, from about 50 nm to about 1000 nm, from about 100 nm to about 1000 nm, from about 200 nm to about 1000 nm, from about 50 nm to about 500 nm).

In yet another aspect, the invention generally relates to a method for controlled delivery of an agent to a target biological site. The method includes: providing a composition comprising a gel composition of cross-linked hyaluronic acid as a host network and an agent selected from therapeutic, diagnostic, or imaging agents encapsulated therein; delivering the composition to the target biological site; and causing a partial or complete de-crosslinking of the host network resulting in release of the agent therefrom.

In yet another aspect, the invention generally relates to a method for controlled delivery of an agent to a target biological site. The method includes: providing a pharmaceutical composition comprising a di-ester of methotrexate disclosed herein; delivering the pharmaceutical composition to the target biological site; and causing a partial or complete de-crosslinking of the host network resulting in release of the agent therefrom at the target biological site.

In yet another aspect, the invention generally relates to a method for treating or diagnosing a disease or condition. The method includes: administering to a subject in need thereof a therapeutically effective amount of a composition comprising a gel composition of cross-linked hyaluronic acid as a host network and an agent selected from therapeutic, diagnostic, or imaging agents encapsulated therein, optionally with a pharmaceutically acceptable carrier or excipient.

In yet another aspect, the invention generally relates to a method for treating a disease or condition. The method includes: administering to a subject in need thereof a therapeutically effective amount of a pharmaceutical composition disclosed herein.

In certain embodiments, the method is useful for treating a CD44 positive cell mediated disease, or a related condition.

CD44 positive cell mediated diseases include the autoimmune conditions, Rheumatoid Arthritis, Systemic Lupus Erythematosus, Multiple Sclerosis, Type 1 Diabetes, Juvenile Idiopathic Rheumatoid Arthritis, Uveitis and Aplastic Anemia, and certain cancers including, but not limited to, breast cancer, melanoma, prostate cancer, non-small cell lung cancer, lymphoma, and leukemia.

In certain embodiments, the disease or condition is an immune-mediated disease.

In certain embodiments, the disease or condition is selected from rheumatoid arthritis, osteoarthritis, juvenile idiopathic arthritis, uveitis, or other CD44-mediated autoimmune condition.

In certain embodiments, the disease or condition is rheumatoid arthritis.

In certain embodiments, the disease or condition is cancer.

In certain embodiments, the subject being treated suffers from methotrexate resistance.

Any suitable method of administration may be employed. In certain embodiments, administration is systemic. In certain embodiments, administration is local.

In certain embodiments, administration is by injection.

In certain embodiments, administration is by injection into the synovial space of at least one disease-affected joint, intra-articular injection or intravenous injection or intradermal injection.

In certain embodiments of the treatment method, the agent is a di-ester of methotrexate having the structural formula:

wherein each R is independently selected from the group consisting of aliphatic group and aryl group.

In certain embodiments, at least one R is an aliphatic group.

In certain embodiments, each R is an aliphatic group.

In certain embodiments, at least one R is an aryl group.

In certain embodiments, each R is an aryl group.

In certain embodiments, each R is a benzyl group.

In certain embodiments, one R is an aliphatic group and one R is an aryl group.

In certain embodiments, the di-ester of methotrexate is characterized by a log P in the range from about 1.5 to about 10 (e.g., from about 1.5 to about 10, from about 2.0 to about 10, from about 2.5 to about 10, from about 2.0 to about 10, from about 3.5 to about 10, from about 4.0 to about 10, from about 4.5 to about 10, from about 5.0 to about 10, from about 6.0 to about 10, from about 7.0 to about 10, from about 8.0 to about 10, from about 1.5 to about 4.0, from about 4.0 to about 9.0, from about 5.0 to about 9.0, from about 6.0 to about 9.0).

In certain embodiments, the di-ester of methotrexate is encapsulated in a network of cross-linked hyaluronic acid. In certain embodiments, one than one (e.g., two different) di-esters of methotrexate is encapsulated in a network of cross-linked hyaluronic acid.

In certain embodiments, the di-ester of methotrexate is releasable upon partial or complete de-crosslinking of the network of cross-linked hyaluronic acid when delivered to a biological site.

In certain embodiments, from about 1% to about 100% (e.g., from about 10% to about 100%, from about 20% to about 100%, from about 30% to about 100%, from about 40% to about 100%, from about 50% to about 100%, from about 70% to about 100%, from about 90% to about 100%) of the di-ester of methotrexate is released at the biological site.

In yet another aspect, the invention generally relates to a method for making a gel. The method includes: (a) reacting hyaluronic acid with a compound having the structure formula V:

R—C(=CH$_2$)—C(=O)—O—C(=O)—C(=CH$_2$)—R (V)

wherein each R is independently selected from the group consisting of H, $C_1$-$C_{14}$ alkyl group, and halogen; and (b) reacting the product of (a) with a compound having the structural formula:

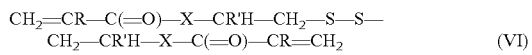

$CH_2$=CR—C(=O)—X—CR'H—$CH_2$—S—S—$CH_2$—CR'H—X—C(=O)—CR=$CH_2$ (VI)

wherein each R' is H or —C(=O)O—R", wherein R" is a group comprising a $C_1$-$C_{14}$ alkyl group or a $C_4$-$C_{14}$ aryl moiety; each X is independently selected from NH, O and S.

In certain embodiments, at least one X is NH. In certain embodiments, each X is NH.

In certain embodiments, at least one X is O or S. In certain embodiments, each X is O or S. In certain embodiments, each X is O. In certain embodiments, each X is S.

In certain embodiments, one X is NH and the other X is O. In certain embodiments, one X is NH and the other X is O.

The Rs may be identical or different. In certain embodiments, each R is H. In certain embodiments, each R is independently a $C_1$-$C_{14}$ alkyl group. In certain embodiments, each R is independently a $C_1$-$C_6$ alkyl group. In certain embodiments, R is independently a $C_1$-$C_3$ alkyl group. In certain embodiments, R is independently a $C_4$-$C_6$ alkyl group. In certain embodiments, the Rs are identical. In certain embodiments, the Rs are different.

The R's may be identical or different. In certain embodiments, each R' is H. In certain embodiments, each R' is independently selected from the group consisting of —C(=O)O—R" and —C(=O)—NH—R". In certain embodiments, each R' is —C(=O)O—R". In certain embodiments, each R' is —C(=O)—NH—R". In certain embodiments, one R' is —C(=O)O—R" and one R' is —C(=O)—NH—R". In certain embodiments, the R's are identical. In certain embodiments, the R's are different.

In certain embodiments, R" is a $C_1$-$C_{14}$ alkyl group. In certain embodiments, R" is a $C_1$-$C_6$ alkyl group. In certain embodiments, R" is independently a $C_1$-$C_3$ alkyl group. In certain embodiments, R is independently a $C_4$-$C_6$ alkyl group. In certain embodiments, the R"s are identical.

In certain embodiments, the R"s are different.

In certain embodiments, R" is a $C_4$-$C_{14}$ aryl moiety. In certain embodiments, R" is independently a $C_4$-$C_6$ aryl moiety. In certain embodiments, R is independently a $C_5$-$C_{10}$ aryl moiety. In certain embodiments, the R"s are identical. In certain embodiments, the R"s are different.

$R_x$ may be any suitable bond providing linkage from the cross-linking group to the crosslinked hyaluronic acid network. In certain embodiments, the bond is a single bond, for example, a C—C single bond, a C-heteroatom single bond (e.g., C—O, C—S, C—N), a C=C double bond, or a C=N double bond.

In certain embodiments of the method for making a gel, the degree of crosslinking may vary. In certain embodiments, the cross-linked hyaluronic acid has a degree of cross-linking from about 1% to about 100% (e.g., from about 1% to about 99%, from about 1% to about 90%, from about 1% to about 80%, from about 1% to about 70%, from about 1% to about 50%, from about 1% to about 30%, from about 1% to about 20%, from about 1% to about 10%, from about 5% to about 100%, from about 10% to about 100%, from about 20% to about 100%, from about 30% to about 100%, from about 50% to about 100%, from about 60% to about 100%, from about 80% to about 100%, from about 95% to about 100%, from about 25% to about 99%, from about 5% to about 50%, from about 10% to about 50%, from about 20% to about 50%, from about 50% to about 99%, from about 50% to about 70%, from about 70% to about 99%, from about 85% to about 99%).

In certain embodiments of the method for making a gel, the molecular weight of the gel composition may vary. In certain embodiments, the starting hyaluronic acid, prior to crosslinking, has a molecular weight from about 1,000 to about 5,000,000 (e.g., from about 5,000 to about 5,000,000, from about 10,000 to about 5,000,000, from about 50,000 to about 5,000,000, from about 100,000 to about 5,000,000, from about 250,000 to about 5,000,000, from about 500,000 to about 5,000,000, from about 1,000,000 to about 5,000,000, from about 2,000,000 to about 5,000,000, from about 1,000 to about 2,000,000, from about 1,000 to about 1,000,000, from about 1,000 to about 500,000, from about 1,000 to about 200,000, from about 1,000 to about 100,000, from about 1,000 to about 50,000, from about 1,000 to about 20,000, from about 1,000 to about 10,000, from about 5,000 to about 2,000,000, from about 20,000 to about 2,000,000, from about 50,000 to about 2,000,000, from about 100,000 to about 2,000,000, from about 500,000 to about 2,000,000).

In certain embodiments of the method for making a gel, the ratios of the different crosslinking groups may be adjusted as appropriate based on the application at hand. In certain embodiments, the ratio of the cross-linking group (I) to the cross-linking (II) is from about 1:10 to about 10:1 (e.g., from about 1:5 to about 5:1, from about 1:4 to about 4:1, from about 1:3 to about 3:1, from about 1:2 to about 2:1, from about 1:1.5 to about 1.5:1, from about 1:1.2 to about 1.2:1, from about 1:1.1 to about 1.1:1, about 1:1).

In certain embodiments, the method for making a gel further includes providing one or more reaction initiators prior to (a), prior to (b), or prior to (a) and prior to (b).

Any suitable reaction initiator may be used, for example, a radical photo-initiator Irgacure 2959 (2-Hydroxy-1-[4-(2-hydroxyethoxy) phenyl]-2-methyl-1-propanone), AIBN, carbonylperoxides such as benzoyl peroxide, benzoin derivatives, benzilketals, acetophenone derivative, o-hydroxyalkylphenones, O-acyl-alpha-oximinoketones, aromatic ketones with alcohol- or amine-based coinitiators, and inorganic perodixes such as peroxydisulfate salts.

In yet another aspect, the invention generally relates to a compound having the structural formula:

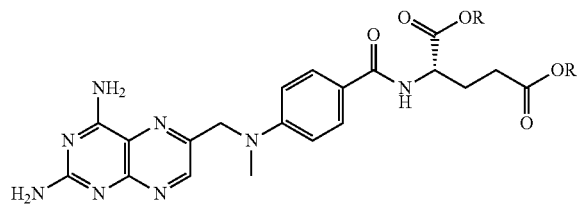

wherein each R is independently selected from the group consisting of aliphatic group and aryl group.

In certain embodiments, at least one R is an aliphatic group.

In certain embodiments, each R is an aliphatic group.

In certain embodiments, at least one R is an aryl group.

In certain embodiments, each R is an aryl group.

In certain embodiments, each R is a benzyl group.

In certain embodiments, one R is an aliphatic group and one R is an aryl group.

In certain embodiments, the di-ester of methotrexate is characterized by a log P in the range from about 1.5 to about 10 (e.g., from about 1.5 to about 10, from about 2.0 to about 10, from about 2.5 to about 10, from about 2.0 to about 10, from about 3.5 to about 10, from about 4.0 to about 10, from about 4.5 to about 10, from about 5.0 to about 10, from about 6.0 to about 10, from about 7.0 to about 10, from about 8.0 to about 10, from about 1.5 to about 4.0, from about 4.0 to about 9.0, from about 5.0 to about 9.0, from about 6.0 to about 9.0).

Examples

I. Synthesis of HA-Decorated Nanoparticles (HA-NP)
Synthesis of Polymer NPs

The synthetic scheme for synthesis of polymer NPs is shown in Scheme 1 (FIG. 13). Preparation of methacrylate-derived HA: 2 g of HA (hyaluronic acid, 13 kDa) was dissolved in 100 mL of deionized (DI) water and stirred at RT overnight, followed by the addition of 1.6 mL of MA (methacrylic anhydride) into the HA solution. The pH of the reaction was maintained between 8 and 9 by adding 5N NaOH and kept at 4° C. under continuous stirring for 24 h. m-HA was precipitated in acetone, washed with ethanol and then dissolved in DI water. After dialysis against DI water for 48 h, the pure product was isolated as a white powder after lyophilization. The degree of modification (DM) was determined to be about 17% by comparing the ratio of the areas under the proton peaks at 5.74 and 6.20 ppm methacrylate protons) to the peak at 1.99 ppm (N-acetyl glucosamine of HA).

Encapsulation of Active Drug

The synthetic scheme for encapsulation of active drug is shown in Scheme 2 (FIG. 14). To a solution of MTX (200 mg, 0.44 m·mol) in benzyl alcohol (10 mL) was added DMAP (21.5 mg, 0.176 m·mol) at RT. The reaction mixture was stirred at RT for 10 mins and then cooled to 0° C. To the cooled solution, DCC (182 mg, 0.88 m·mol) was added. The RM was then kept at 40° C. for 90 h. Afterwards, it was concentrated under reduced pressure and the residue was dissolved in DCM (30 mL) and washed with sat'd NaHCO$_3$ and brine solution. The organic layer was separated and dried with MgSO$_4$ and filtered. The crude product was purified by column chromatography (9:1 MeOH:DCM) to yield MMTX (128 mg, 46%) as a yellow powder: ESIMS: m/z=635.2704 [M+H]$^+$ (m/z calcd. for C$_{34}$H$_{35}$N$_8$O$_5$=635.2725); $^1$H NMR (400 MHz, DMSO-d6, TMS): δ (ppm)=1.97-2.17 (2H, m), 3.21 (3H, s), 4.45-4.50 (1H, m), 5.11 (2H, s), 6.61 (2H, bs), 6.81-6.83 (2H, d, 8 Hz), 7.29-7.33 (10H, m), 7.43-7.65 (2H, bs), 7.71-7.74 (2H, d, 12 Hz), 8.37-8.39 (2H, d, 8 Hz), 8.57 (1H, s). $^{13}$C NMR (400 MHz, DMSO-d6, TMS): S (ppm)=25.7, 30.1, 51.9, 54.8, 65.5, 65.8, 111.0, 120.8, 121.4, 127.6, 127.7, 127.8, 127.9, 128.3, 128.4, 129.0, 136.0, 136.1, 145.9, 149.1, 151.0, 155.2, 162.7, 162.8, 166.6, 171.9, 172.1.

A suspension of modified HA from above (1 mg/mL), crosslinker N,N'-bis(acryloyl) cystamine (10 mg) and 2-hydroxy-4'-(2-hydroxyethoxy)-2-methylpropiophenone (Irgacure 2959) (5 mg) in water (10 mL) was stirred at RT for 30 min. and purged with argon for 15 min. After which 1 mL of this solution was transferred into a vial. To this solution, the encapsulant molecule (e.g. Nile red (50 μL, 1 mg/mL in acetone)) was added. The reaction mixture was exposed to UV irradiation (365 nm) for 0 min. (control) or 10 min. (Nile red encapsulated). Afterwards, the reaction mixture was stirred overnight at RT in an open vial to evaporate acetone from the solution and filtered through a hydrophilic membrane (pore size: 0.45 μm) to remove free, unencapsulated guest molecule from the solution.

Figure 1:
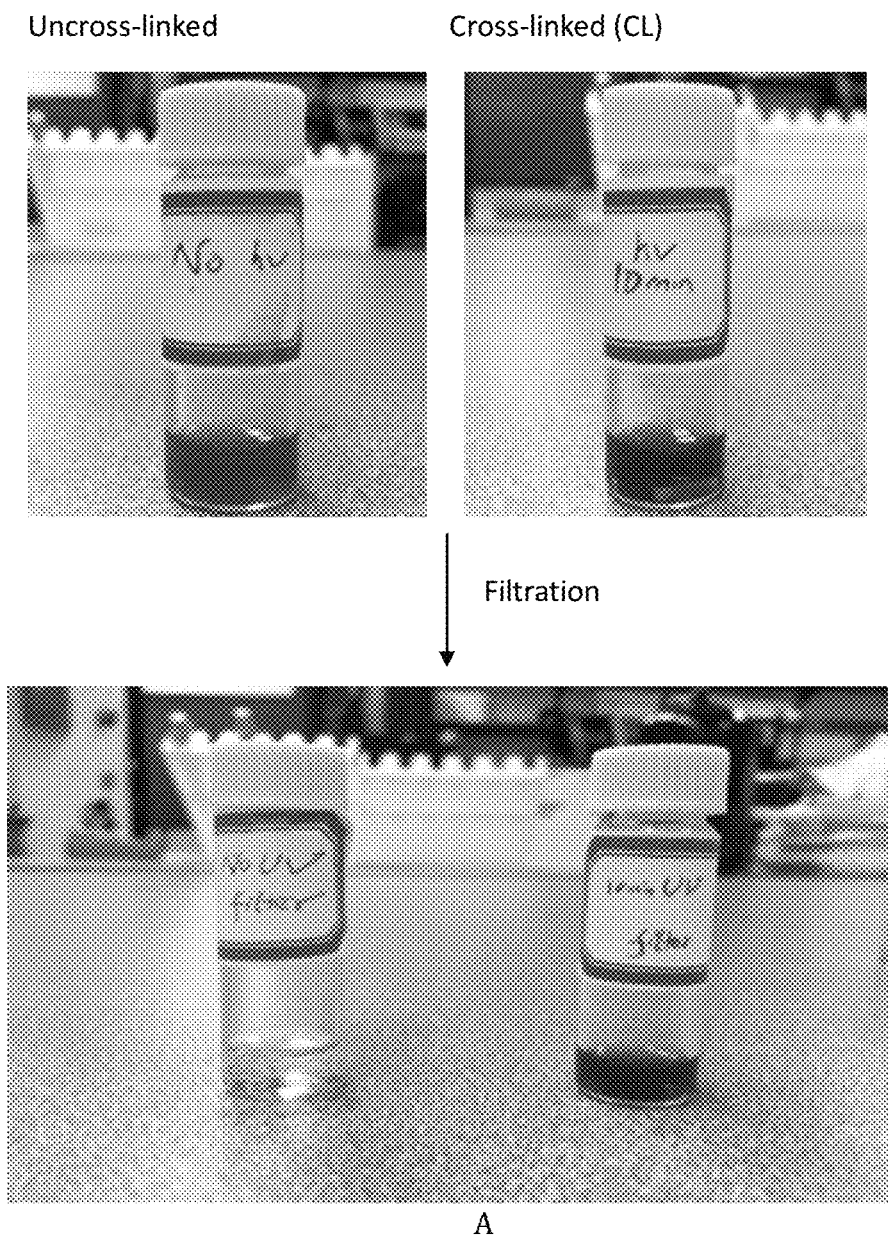
FIG. 1. Synthesis of HA-decorated nanoparticles. (A) Illustration of the encapsulation of a hydrophobic dye in crosslinked HA-decorated nanoparticles. When no photo-initiated crosslinking is carried out, the dye molecules are not encapsulated and are therefore filtered out of the solution (left).
Figure 1:
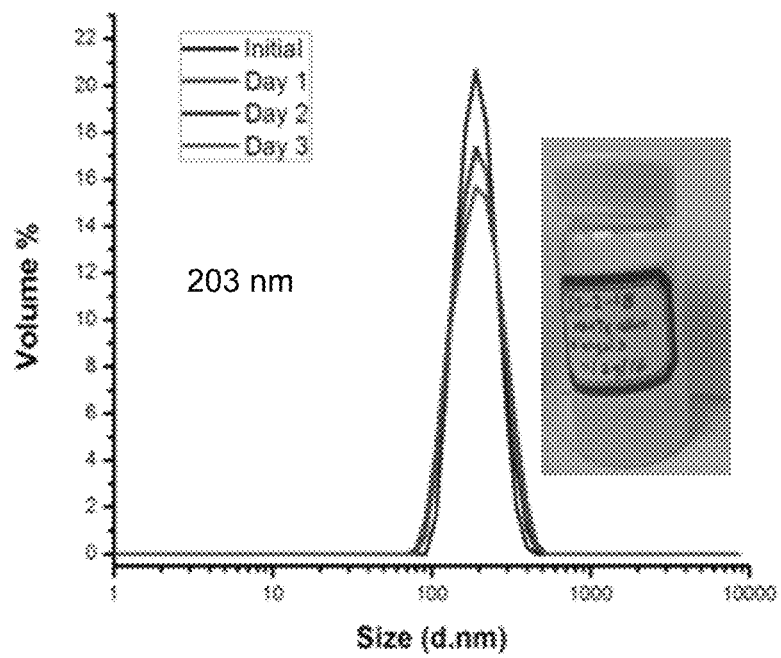
Figure 1:
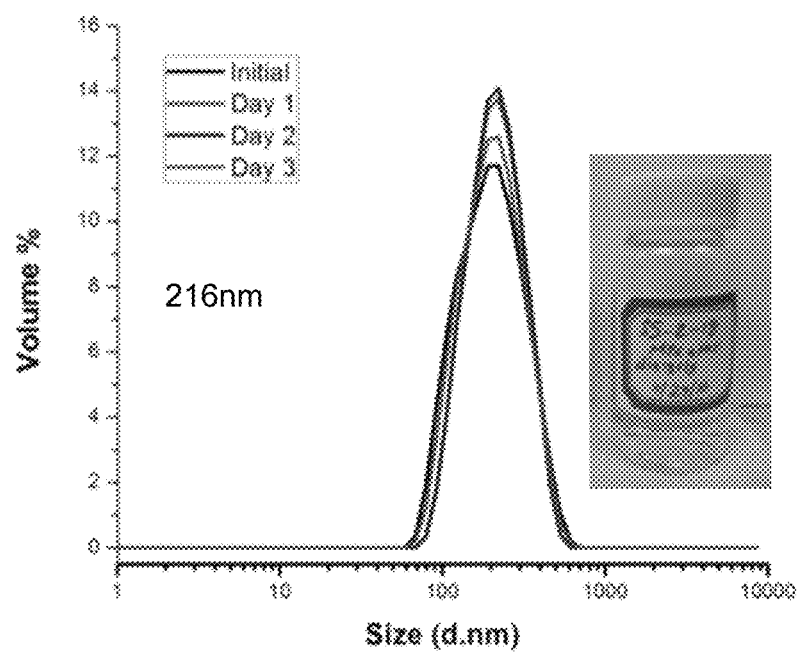

The ability of these nanoparticles to encapsulate Nile red was evaluated using spectroscopic measurements. The resultant polymeric complex was evaluated at different exposure levels of light for the polymerization. It was found that the encapsulation to consistently increase with the amount of exposure time with the near maximum encapsulation occurring at 10 min irradiation, as shown in FIG. 1.

These Nile red-loaded nanoparticles were evaluated for uptake by CD44 cells. The uptake was shown to be efficient in CD44-rich cells. Comparison of cellular uptake at 4° C. vs 37° C. would show that it is an activated uptake (FIG. 2A). Furthermore, the cellular uptake was also evaluated in the presence of an inhibitor that blocks CD44-mediated uptake. In this case, the uptake was substantially reduced. These results indicate that the uptake is indeed CD44-mediated (FIG. 2B). After additional control experiments to confirm for receptor mediated uptake, these nanoparticles were chosen as the candidate for further evaluation.

MTX and MMTX encapsulation: A suspension of modified HA (1 mg/mL), crosslinker (2 mg/mL) and Irgacure 2959 (0.5 mg/mL) in water (1 mL) was stirred at RT for 30 mins and purged with argon for 10 mins. To this solution, MTX (100 μL, 6 mg/mL) or MMTX (100 μL, 6 mg/mL) or DMSO 100 μL (control) was added. The reaction mixture was exposed to UV irradiation for 10 min. Afterwards, the free drug was removed by dialyzing the solution against DI water for 48 h and filtered through a hydrophilic membrane (pore size: 0.45 μm). The resulting solution was used to estimate the size of the drug loaded PNPs using dynamic light scattering.

Calculation of drug loading efficiency and loading capacity: The drug loading efficiency (DLE) and drug loading capacity (DLC) were calculated by absorption spectroscopy using the following equations:

DLE (%)=[weight of drug in PNPs/weight of drug in feed]×100%

DLC (%)=[weight of drug in PNPs/weight of drug loaded PNPs]×100%

The drug loading capacity and drug loading efficiency of the MMTX loaded NPs were found to be 28.3% and 47.2% respectively. The drug loading capacity and drug loading efficiency of the MTX loaded NPs were found to be 0.062% and 0.10% respectively. The weight of the drug in PNPS for MTX and MMTX was estimated from a calibration curve obtained by looking at the MTX and MMTX absorbance at 372 nm in DMSO/water and at 388 nm in DMSO respectively.

FIG. 1 shows exemplary results of synthesis of HA-decorated nanoparticles.

II. Quantify Specific, CD44 Receptor-Mediated Cellular Uptake of HA-NP Using a Variety of In Vitro Culture Assays
In Vitro Testing System to Evaluate the Interactions of HA-NP with CD44 Receptor The mouse thymoma cell line, BW-5741, which constitutively expresses high levels of CD44, was used to demonstrate HA-NP uptake is an active process. BW-5741 cells were obtained from the American Type Culture Collection (ATC; Manassas, VA) and grown in culture in accordance with ATCC recommendations. HA-FITC polymeric nanoparticle were synthesized with fluorescein-isothyiocyanate-tagged hyaluronic acid (HA; MW=250 kD). HA-FITC-polymeric nanoparticles were incubated with BW-5741 cells at 4° C. or at 37° C. for 30 minutes. At the end of this incubation time, cells were washed vigorously with an established wash protocol designed to shed any HA-FITC polymeric nanoparticles bound to the cell surface. Fluorescence intensity of internalized HA-FITC polymeric nanoparticles was determined by flow cytometry using a BD Fortessa-LSR Flow Cytometer (Becton-Dickinson, Franklin Lakes, NJ). HA-FITC-polymeric nanoparticles internalized by cells, were excited using the 488 nm argon laser and fluorescence emission was collected at 521 nm.

FIG. 2 shows the characterization data of receptor-mediated uptake of HA-FITC-decorated polymeric nanoparticles. FIG. 2A shows BW-5741 cells incubated with HA-FITC-polymeric nanoparticles at 4° C. showed no intracellular uptake detected at the end of the 4-hour incubation period. FIG. 2B shows that approximately 78% of cells incubated with HA-FITC-polymeric nanoparticles at 37° C., were FITC-positive, indicating that cellular uptake of HA-FITC polymeric nanoparticles is an active process, and consistent with receptor-mediated endocytosis.

To confirm cellular uptake was mediated via the CD44 receptor, HA-FITC-polymeric nanoparticles were incubated with PEP-1 (GAHWQFNALTVR), a small peptide that binds to HA and prevents its subsequent interactions with the CD44 receptor. Compared to HA-FITC polymeric nanoparticles that were not incubated with Pep-1 (FIG. 2C), incubating HA-FITC polymeric nanoparticles with Pep-1 (FIG. 2D) reduced its intracellular uptake by BW-5741 cells by approximately 75%. Thus, intracellular uptake of HA-FITC polymeric nanoparticles is an active process and can be inhibited when the HA-CD44 site of interaction is blocked by pre-incubation with PEP-1.

Quantification of CD44 Expression on Mouse and Human Immune Cells

Flow cytometry was used to assess CD44 expression on stimulated bulk splenocytes, CD4 and CD8 T cell and on in vitro polarized Th1 and Th17 cells.

Six to eight-week-old C57BL/6 mice were humanely euthanized following protocols approved by the Institutional Care and Use Committee at the University of Massachusetts. Spleens were removed, antiseptically, and dissociated in sterile phosphate buffered saline using the flat end of a 3 ml syringe. Cell suspension was then passed through a 40-micron filter. Tissue culture wells of a 12-well plate were coated overnight at 4° C. with purified hamster anti-mouse CD3ε (BD Biosciences, San Jose, CA) plus purified NA/LE hamster anti-mouse CD28 (BD Biosciences). $1\times10^6$ cell/ml were plated in 1 mL culture media onto single wells of a 12-well tissue culture plate, pre-coated with antibodies. Cells were incubated for 48-72 hours at 37° C. At the end of the culture period, cells were stained with Phycoerythrin-conjugated-anti-mouse/human CD44 (BioLegend, San Diego, CA) only, or co-stained for CD4 and CD44 or for CD8 and CD44.

The results shown in FIG. 3 indicate that CD44 expression is increased on activated and differentiated murine T cells. FIG. 3A shows that approximately 75% of bulk splenocytes expressed CD44 after 48 hours of stimulation, while approximately 80% of stimulated CD4 T cells expressed CD44 after 48 hours of stimulation (FIG. 3B) and 100% of stimulated CD8 T cells expressed CD44 following 72 hours of culture (FIG. 3C).

To polarize cells towards a T helper type 1 (TH1) or a T helper type 17 (TH17) phenotype, murine primary CD4 T cells were purified using the IMAG separation system, following the manufacturer's protocol (BD Biosciences). Purified CD4 T cells were cultured under conditions that enhanced differentiation towards a TH1 phenotype (IL-12 [1 ng/mL final concentration] plus anti-IL4 [10 μg/mL final concentration; both BioLegend]) or a TH17 phenotype (+TGFβ+IL-6). Greater than 99% of TH1 (FIG. 3D) and TH17 (FIG. 3E) cells express CD44 after 72 hours of culture under polarizing conditions. These data confirm that CD44 is upregulated on primary T cells after 48-72 hours of stimulation under non-polarizing conditions as well as under conditions that promote TH1 or TH17 differentiation.

Baseline Readouts for Activated and Polarized Cells

Flow cytometry was used to assess IFNγ production by stimulated and Th1-polarized CD4 T cells. Data on baseline expression of the TH1 pro-inflammatory cytokine, interferon gamma (IFNγ) using intracellular staining approaches and flow cytometry are presented in FIG. 3. $1\times10^6$ cell/mL were plated in 1 mL culture media onto single wells of a 12-well tissue culture plate, pre-coated with antibodies (FIG. 4A) or cultured in conditions favoring TH1 differentiation (FIG. 4B), as described. Cells were cultured for 72 hours at 37° C. TH1-polarized cells were lifted, washed and restimulated on antibody-coated plates for 5 hours in the presence of 0.67 mL of Golgi-Stop (BD Biosciences)/mL of culture medium. At the end of the additional culture time, cells from each culture condition were lifted, washed in FACS staining buffer, and permeabilized using the FoxP3 Fix/Perm Buffer Set (BioLegend), following the manufacturer's protocol. Cells were incubated with Allophycocyanin (APC)-conjugated rat anti-mouse-IFNγ (BD Biosciences) in Fix/Perm (0.5 μL antibody/50 μL Fix/Perm Buffer) for 30 minutes at 4° C. Following intracellular staining, cells were washed in Fix/Perm buffer and fluorescence was measured in the 642-745 nm range using a BD Fortessa Dual Flow Cytometer (BD Biosciences). Following 72 hours of stimulation alone, low levels of intracellular IFNγ, could be detected (FIG. 4A). Detection of intracellular IFNγ was much greater for CD4 T cells cultured under TH1 polarizing conditions (FIG. 4B).

Characterization of HA-NP:NileRed Delivery In Vitro

Imaging flow cytometry was used to assess HA-NP: NileRed cellular uptake in stimulated CD4 and CD8 T cells.

FIG. 5 shows that Nile Red-loaded HA polymeric nanoparticles are internalized by primary murine CD4 and CD8 T cells, as determined by imaging flow cytometry. Primary murine CD4 and CD8 T cells were purified using the IMAG separation system, following the manufacturer's protocol (BD Biosciences). Purified cell subsets were stimulated for 24 hours on tissue culture plates pre-coated with anti-CD3ε□ and anti-CD28, as described. Stimulated cells were incubated for an additional 40 hours at 37° C. in the presence of HA polymeric nanoparticles loaded with the lipophyllic fluorophore, Nile Red. At the end of the 40-hour incubation period, cells were lifted and washed three times using FACS wash buffer. Cells were stained with APC-conjugated anti-mouse/human CD44 surface and analyzed using an Amnis Image Stream (END Millipore, Billerica, MA).

Following incubation with Nile Red-loaded HA-NPs, >60% of stimulated CD4 T cells showed Nile Red internalization (FIG. 5A) and >90% of stimulated CD8 T cells showed Nile Red internalization (FIG. 5B). Image acquisition was performed using a 60× magnification for all samples with a minimum of 3,000 cells analyzed for each sample. Nile Red fluorescence (from channel three; 560-595 nm), APC fluorescence (from channel five; 642-745 nm) and bright field images (from channel four) were collected as CIF files. Data files (CIF files) were analyzed using the IDEAS software platform (END Millipore). Samples were compensated using a compensation matrix generated using single marker stains. The compensated population was then gated to eliminate cells that were not in the field of focus, were doublets or were considered cell debris.

The IDEAS software internalization wizard was used to measure internalization scores. The internalization wizard uses an algorithm that defines internalization based on the ratio of the fluorescence intensity inside the cell to the fluorescence intensity of the entire cell. The software calculates internalization scores by creating a cytosol mask eroded in from the cell membrane mask. Briefly, a cell membrane mask is defined by the image obtained from surface staining (i.e., APC-conjugated anti-CD44 image). By using these generated masks (cytosol mask and entire field view mask), the wizard calculates internalized Nile Red. The wizard eliminates the Nile Red signal present on and outside of the cell membrane. Internalization of Nile Red, mediated by HA polymeric nanoparticles uptake, shows that after two hour's incubation.

Uptake of HA-NP: (mMTX)

FIG. 6 shows that modified methotrexate-loaded HA polymeric nanoparticles cause dose-dependent cytotoxicity in stimulated primary murine CD4 and CD8 T cells, and in CD4 TH1 cells. Methotrexate (MTX) is known to have cytotoxic effects, in part through its inhibition of cellular purine metabolism, and has been shown to increase apoptosis in activated T cells. Thus, cellular viability was used as a readout of HA polymeric nanoparticle delivery of the modified form of MTX (mMTX).

Primary murine CD4 T cells or CD8 T cells were stimulated for 24 hours on antibody pre-coated plates as described. In a separate experiment, primary murine CD4 T cells were differentiated, in vitro, towards a TH1 phenotype for 24 hours, as described. At the end of 24 hours, HA polymeric nanoparticles, loaded with modified methotrexate (mMTX), was added to all wells. Cells were incubated for an additional 40 hours, at which time they were lifted, washed and stained with Zombie Violet Fixable Viability kit (BioLegend), following the manufacturer's protocol. Cells were then stained with phycoerytherin-conjugated Annexin V, using the PE Annexin V Apoptosis Detection Kit I (BD Biosciences), following the manufacturer's instructions. Cells were analyzed using a BD Fortessa Dual Flow Cytometer (BD Biosciences).

Data from at least 10,000 cells/condition were acquired. Data are displayed in frequency histograms showing percentages of CD4 T cells (FIG. 6A), CD8 T cells (FIG. 6B) or CD4 TH1-polarized cells (FIG. 6C) staining negative for Annexin V, after incubation with increasing concentrations of mMTX/million cells. (NP=polymeric nanoparticles only; MMNP=HA polymeric nanoparticle, loaded with mMTX; NP-Stimulated=cells stimulated on anti-body-pre-coated plates, incubated with empty polymeric nanoparticles; NP-TH1=cells differentiated towards a TH1 phenotype, incubated with empty polymeric nanoparticles).

Observed was decreasing cell viability with increasing concentration of mMT, delivered intracellularly using polymeric nanoparticles. It was found that this effect was similar in stimulated primary murine CD4 (FIG. 6A) and CD8 T cells (FIG. 6B), as well as in primary murine TH1-polarized CD4 T cells (FIG. 6C).

$IC_{50}$ of MMNPs (mMTX) as an Intracellularly-Delivered Cargo

The $IC_{50}$ of MMNPs (mMTX) was determined for a variety of cell types. FIG. 7 shows the $IC_{50}$ of the modified methotrexate delivered intracellularly by HA polymeric nanoparticles.

In FIG. 7A, the percentage of live TH1 cells, determined as described, was plotted against the increasing concentration of mMTX in HA polymeric nanoparticles delivered to these cells following TH1 polarization and an additional 40-hour incubation. FIG. 7B shows median fluorescence intensity of intracellular IFNγ, determined as described, plotted against the increasing concentration of mMTX in HA polymeric nanoparticles delivered to these cells following TH1 polarization and an additional 40-hour incubation. FIG. 7C displays a table showing $IC_{50}$ of several cell types calculated by plotting percentage of live cells, determined as described, plotted against the increasing concentration of mMTX in HA polymeric nanoparticles delivered to these cells following culture (BW cells), stimulation for 24 hours (CD8, CD4 cells) or TH1 polarization for 24 hours (TH1 cells) followed by an additional 40-hour incubation with mMTX-loaded polymeric nanoparticles.

Rat Model of RA for In Vivo Testing

AIA was induced in 6-week-old Lewis rats and followed weight change and disease course for 30 days to establish baseline values. FIG. 8 shows that intra-articular injection of HA polymeric nanoparticles attenuate disease in a rat model of Adjuvant-Induced Arthritis (AIA).

AIA was induced by injecting 50 to 100 µL of Complete Freund's Adjuvant (M. tuberculosis H-37; 10 mg/mL) via intradermal injection at the base of the tail of 7-week old male Lewis rats. Beginning on day +11 rats were weighed daily and disease severity was scored daily, using a standardized scoring system: Each digit of each limb was scored as follows: 0=No arthritis; 0.1=redness or swelling. Each large joint of each limb was scored as follows: 0=no arthritis; 0.5=mild, but definite, redness or swelling; 1.0=severe redness or swelling. Scores from digits and joints were added together to give a total score (range 0-5.8) for each day the animal was observed. Scores were recorded from day +11 through day +30, at which point animals were removed from the study by humane euthanasia.

Tested was the ability of mMTX, delivered in HA polymeric nanoparticles via intra-articular injection, to modulate disease severity under three dosing regimens, compared to animals who received no treatment (n=8; blue columns and trend bar). Treatment #1 (n=1; orange columns and trend lines): animals received a single injection of 2 µL of ~mMTX-loaded HA polymeric nanoparticles (~0.4 µg mMTX) resuspended in a total of 50 µL sterile phosphate buffered saline delivered via intra-articular injection in the left knee on day +8 and a single injection of 1.2 µL of MTX-loaded polymeric nanoparticles (~0.24 µg mMTX) resuspended in a total of 30 µl sterile phosphate buffered saline delivered via intra-articular injection on day +15. Treatment #2 (n=3; grey columns and trend bars): animals received a single injection of 1.2 µL of ~mMTX-loaded HA polymeric nanoparticles (~0.24 µg mMTX) resuspended in a total of 30 µL sterile phosphate buffered saline delivered via intra-articular injection in the left knee on day +8 and a single injection of 2 µL of MTX-loaded polymeric nanoparticles (~0.4 µg mMTX) resuspended in a total of 50 µL sterile phosphate buffered saline delivered via intra-articular injection on day +15. Treatment #3 (n=3; yellow columns and trend bars): animals received a single injection of 3 µL of ~mMTX-loaded HA polymeric nanoparticles (~0.6 µg mMTX) resuspended in a total of 30 µL sterile phosphate buffered saline delivered via intra-articular injection in the left knee on day +8. Data are representative of 1-8 animals per condition±SD.

Inhibitory Effects on Disease Progression

The results shown in FIG. 9 indicate that intra-articular delivery of mMTX-loaded HA polymeric nanoparticles attenuates swelling in a rat model of AIA.

AIA was induced in 7-week old male Lewis rats, as described. On day +8 after induction, approximately 2 µL of HA polymeric nanoparticles containing approximately 0.4 µg of mMTX was suspended in a total of 50 µL of sterile phosphate buffered saline, and injected into the left knee of treated rats. On day +20 after AIA induction, arthritis progression was documented in the fore limbs and hind limbs of (FIG. 9A) negative control animals (no disease induction), (FIG. 9B) animals induced with AIA but not receiving treatment, or (FIG. 9C) animals induced with AIA and receiving a single intra-articular injection of HA polymeric nanoparticles loaded with mMTX.

Representative images of negative control animal (no disease induction) (FIG. 9A) showing normal appearance of i) left hind limb, side view; ii) left front paw, pads; iii) left hind foot, pads; animal with AIA showing appearance of arthritis (FIG. 9B) in i) left hind limb, side view; ii) left front paw, pads; iii) left hind foot, pads; animal with AIA treated with a single intra-articular injection of HA polymeric nanoparticles pre-loaded with mMTX, showing near-normal appearance of i) left hind limb, side view; ii) left front paw, pads; iii) left hind foot, pads (FIG. 9C).

Extended Quantitative Physical Assessment of Disease Progression Following Intra-Articular Delivery of and Cellular Uptake of HA-NP in the AIA Rat Model of RA AIA was induced by injecting 50 to 100 μl of Complete Freund's Adjuvant (*M. tuberculosis* H-37; 10 mg/mL) via intradermal injection at the base of the tail of 7-week old male Lewis rats. Beginning on day +11 rats were weighed daily and disease severity was scored daily, using a standardized scoring system: Each digit of each limb was scored as follows: 0=No arthritis; 0.1=redness or swelling. Each large joint of each limb was scored as follows: 0=no arthritis; 0.5=mild, but definite, redness or swelling; 1.0=severe redness or swelling. Scores from digits and joints were added together to give a total score (range 0-5.8) for each day the animal was observed. Scores were recorded from day +11 through day +30, at which point animals were removed from the study by humane euthanasia. We tested the ability of mMTX, delivered in HA polymeric nanoparticles via intra-articular injection, to modulate disease severity under three dosing regimens, compared to animals who received no treatment (n=8; blue columns and trend bar). Collated data from all treatment regimens are shown. Treatment #1 (n=1; orange columns and trend lines): animals received a single injection of 2 μL of mMTX-loaded HA polymeric nanoparticles (~0.4 μg mMTX) resuspended in a total of 50 μL sterile phosphate buffered saline delivered via intra-articular injection in the left knee on day +8 and a single injection of 1.2 μL of MTX-loaded polymeric nanoparticles (~0.24 μg mMTX) resuspended in a total of 30 μl sterile phosphate buffered saline delivered via intra-articular injection on day +15. Treatment #2 (n=3; grey columns and trend bars): animals received a single injection of 1.2 μL of mMTX-loaded HA polymeric nanoparticles (~0.24 μg mMTX) resuspended in a total of 30 μL sterile phosphate buffered saline delivered via intra-articular injection in the left knee on day +8 and a single injection of 2 μL of MTX-loaded polymeric nanoparticles (~0.4 μg mMTX) resuspended in a total of 50 μL sterile phosphate buffered saline delivered via intra-articular injection on day +15. Treatment #3 (n=3; yellow columns and trend bars): animals received a single injection of 3 μl of mMTX-loaded HA polymeric nanoparticles (~0.6 μg mMTX) resuspended in a total of 30 μl sterile phosphate buffered saline delivered via intra-articular injection in the left knee on day +8. Treatment #4 (n=6) Treatment #5 (n=6; dark orange columns and trend bars): animals received a single injection of 20 μL of mMTX-loaded HA polymeric nanoparticles (~3.6 μg mMTX; ~3×$IC_{50}$) resuspended in a total of 50 μL sterile phosphate buffered saline delivered via intra-articular injection in the left knee on day +8. Treatment #5 (n=6; purple columns and trend bars): animals received a single injection of 20 μL of mMTX-loaded HA polymeric nanoparticles (~3.6 μg mMTX; ~3×$IC_{50}$) resuspended in a total of 50 μL sterile phosphate buffered saline delivered via intra-articular injection in the left knee on day +17. Data are representative of 1-8 animals per condition±SD. (FIG. 10.) Assessment of systemic disease (endpoint analysis)

Cytokine levels assessed on day +22 do not correlate closely with clinical score following intra-articular delivery of mMTX-loaded HA polymeric nanoparticles in a rat model of Adjuvant-Induced-Arthritis (AIA). Disease was induced in 7-week old male Lewis rats, as described. On day +8, or on day +17 after induction, approximately 20 μL of HA polymeric nanoparticles containing approximately 3.16 μg of mMTX was suspended in a total of 50 μl of sterile phosphate buffered saline and injected into the left knee of treated rats. On day +22 after AIA induction, arthritis progression was documented in the in fore limbs and hind limbs, and animals were humanely euthanized. Blood was obtained immediately upon euthanasia via cardiac puncture and collected into heparin-coated syringes. Samples were spun at 2500 rmp in a table top centrifuge for 7 minutes at 20° C. and plasma was removed from red cells and stored at −80° C. until analyzed. Plasma cytokine levels for (A) IL-6, (B) TNF, and (C) IL-1β, were determined using standard ELISA techniques (RayBiotech) following the manufacturer's instructions. Absorbance was read at 450 nm after the addition of stop solution using a BioTech Plate Reader. Cytokine concentrations (pg/ml) were calculated against standard curves of known concentrations generated for each cytokine measured. (FIG. 11.)

Histological Assessment of Localized Disease (Endpoint Analysis)

Cellular infiltration on day +22 does not correlate closely with clinical score following intra-articular delivery of mMTX-loaded HA polymeric nanoparticles in a rat model of AIA. Disease was induced in 7-week old male Lewis rats, as described. On day +8, or on day +17 after induction, approximately 20 μL of HA polymeric nanoparticles containing approximately 3.5 μg of mMTX was suspended in a total of 50 μL of sterile phosphate buffered saline, and injected into the left knee of treated rats. On day +22 after AIA induction, arthritis progression was documented in the in fore limbs and hind limbs, and animals were humanely euthanized. Knee joints of untreated treated and treated animals were dissected out, fixed and decalcified overnight in CalRite Decalcifying solution (Formic acid and 10% [v/v] Formalin in Phosphate Buffered Saline). Knee joints were rinsed in 70% EtOH, and transported to Pioneer Valley Life Sciences Institute, where they were processed, paraffin-embedded, sectioned and stained with Hematoxylin and Eosin. FIG. 12 (A, H) Knee joints from one animal induced with AIA but not receiving treatment; FIG. 12 (B-G) knee joints from animals induced with AIA and receiving a single intra-articular injection into the left knee of HA polymeric nanoparticles loaded with mMTX on day +8, FIG. 12 (I-N) animals induced with AIA and receiving a single intra-articular injection into the left knee of HA polymeric nanoparticles loaded with mMTX on day +17.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise. Unless defined otherwise, all technical and scientific terms used herein have the same meaning as commonly understood too one of ordinary skill in the art. Unless defined otherwise, all technical and scientific terms used herein have the same meaning as commonly understood by one of ordinary skill in the art. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A gel composition comprising cross-linked hyaluronic acid, wherein the hyaluronic acid is cross-linked by one or more cross-linking groups that comprises structural formula I:

—C(=O)—CR(R$^1$)—CH$_2$—CR(R$^2$)—C(=O)— (I)

and one or more cross-linking groups that comprises structural formula II:

—CH$_2$—S—S—CH$_2$— (II)

wherein each of R, R$^1$ and R$^2$ is independently selected from the group consisting of H, a C$_1$-C$_{14}$ alkyl group, a C$_4$-C$_{14}$ aryl group, a halogen, or a bond linking the cross-linking group to the crosslinked hyaluronic acid network.

2. The gel composition of claim 1, wherein R$^1$ is H and R$^2$ is H, and structural formula I becomes structural formula Ia:

—C(=O)—CRH—CH$_2$—CRH—C(=O)— (Ia).

3. The gel composition of claim 1, wherein the one or more cross-linking groups that comprises structural formula II further comprises a unit of —C(=O)—X—CR'H— covalently bonded to —CH$_2$—S—S—CH$_2$— at each end thereof such that the one or more cross-linking groups that comprises structural formula II comprises the structural formula III:

—C(=O)—X—CR'H—CH$_2$—S—S—CH$_2$—
   CR'H—X—C(=O)— (III)

wherein
each R' is H, —C(=O)O—R", or —C(=O)—NH—R", wherein R" is a group comprising a C$_1$-C$_{14}$ alkyl group or a C$_4$-C$_{14}$ aryl moiety; and
each X is independently selected from NH, O and S.

4. The gel composition of claim 3, wherein at least one X is NH.

5. The gel composition of claim 3, wherein at least one X is O or S.

6. The gel composition of claim 3, wherein the one or more cross-linking groups that comprises structural formula III further comprises a unit of —O—C(=O)— CRR$_x$—CH$_2$—CRR$_x$— covalently bonded to —C(=O)—X—CR'H—CH$_2$—S—S—CH$_2$—CR'H—X—C(=O)— at each end thereof such that the one or more cross-linking groups that comprises structural formula III comprises the structural formula IV:

—O—C(=O)—CRR$_x$—CH$_2$—CRR$_x$—C(=O)—
   X—CR'H—CH$_2$—S—S—CH$_2$—CR'H—X—C
   (=O)—CRR$_x$—CH$_2$—CRR$_x$—C(=O)—O— (IV)

wherein
each R$_x$ independently represents a bond linking the cross-linking group to the crosslinked hyaluronic acid network.

7. The gel composition of claim 6, wherein each R is H.

8. The gel composition of claim 6, wherein each R is a C$_1$-C$_{14}$ alkyl group.

9. The gel composition of claim 3, wherein each R' is H.

10. The gel composition of claim 3, wherein each R' is independently selected from the group consisting of —C(=O)O—R" and —C(=O)—NH—R".

11. The gel composition of claim 10, wherein R" comprises a C$_1$-C$_{14}$ alkyl group.

12. The gel composition of claim 10, wherein R" comprises a C$_4$-C$_{14}$ aryl moiety.

13. A composition comprising a gel composition of cross-linked hyaluronic acid according to claim 1 as a host network and an agent selected from therapeutic, diagnostic, or imaging agents encapsulated therein.

14. A method for controlled delivery of an agent to a target biological site, comprising:
providing a composition according to claim 13 comprising a gel composition of cross-linked hyaluronic acid as a host network and an agent selected from therapeutic, diagnostic, or imaging agents encapsulated therein;
delivering the composition to the target biological site; and
causing a partial or complete de-crosslinking of the host network resulting in release of the agent therefrom at the target biological site.

15. The method of claim 14, wherein the agent
a di-ester of methotrexate has the structural formula:

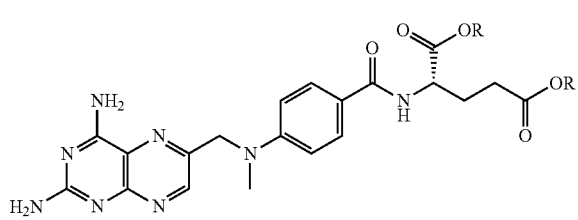

wherein each R is independently selected from the group consisting of aliphatic groups and aryl groups.

16. A method for treating or diagnosing a disease or condition, comprising:
   administering to a subject in need thereof a therapeutically or diagnostically effective amount of a composition according to claim 13 comprising a gel composition of cross-linked hyaluronic acid as a host network and an agent selected from therapeutic, diagnostic, or imaging agents encapsulated therein, optionally with a pharmaceutically acceptable carrier or excipient.

17. A pharmaceutical composition comprising a di-ester of methotrexate and a pharmaceutically acceptable carrier or excipient, wherein the di-ester of methotrexate has the structural formula:

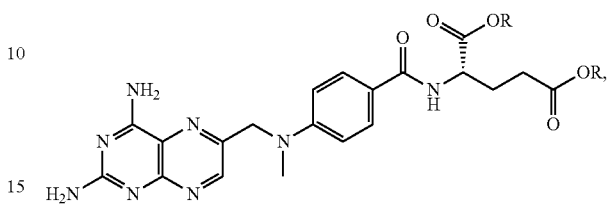

wherein each R is independently an aryl group.

\* \* \* \* \*